(12) United States Patent
Zalay et al.

(10) Patent No.: US 8,315,970 B2
(45) Date of Patent: Nov. 20, 2012

(54) METHOD AND RHYTHM EXTRACTOR FOR DETECTING AND ISOLATING RHYTHMIC SIGNAL FEATURES FROM AN INPUT SIGNAL USING THE WAVELET PACKET TRANSFORM

(75) Inventors: Osbert C. Zalay, Toronto (CA); Berj L. Bardakjian, Toronto (CA)

(73) Assignee: Neurochip Corporation, Ontario (CA)

( * ) Notice: Subject to any disclaimer, the term of this patent is extended or adjusted under 35 U.S.C. 154(b) by 600 days.

(21) Appl. No.: 12/582,563

(22) Filed: Oct. 20, 2009

(65) Prior Publication Data
US 2010/0114813 A1    May 6, 2010

Related U.S. Application Data

(60) Provisional application No. 61/106,944, filed on Oct. 20, 2008.

(51) Int. Cl.
*G06F 17/00*  (2006.01)
*G06F 17/14*  (2006.01)

(52) U.S. Cl. ........... 706/58; 708/317; 708/320; 708/400
(58) Field of Classification Search ............ 706/58
See application file for complete search history.

(56) References Cited

U.S. PATENT DOCUMENTS

| 5,755,671 | A  | 5/1998 | Albrecht et al. |
| 6,434,261 | B1 | 8/2002 | Zhang et al. |
| 6,799,141 | B1 | 9/2004 | Stoustrup et al. |
| 2003/0167003 | A1 | 9/2003 | Masotti et al. |

OTHER PUBLICATIONS

International Search Report and Written Opinion dated Dec. 17, 2009.

*Primary Examiner* — Michael B Holmes
(74) *Attorney, Agent, or Firm* — Harness, Dickey & Pierce

(57) ABSTRACT

A method of detecting and isolating at least one rhythmic component from a discrete-time input signal, comprises subjecting the input signal to discrete wavelet packet transform multi-resolution analysis; applying wavelet packet basis selection criteria to the result of the analysis to evaluate rhythmic signal features of the input signal; and isolating at least one rhythmic signal component from the input signal based on the evaluation.

29 Claims, 19 Drawing Sheets

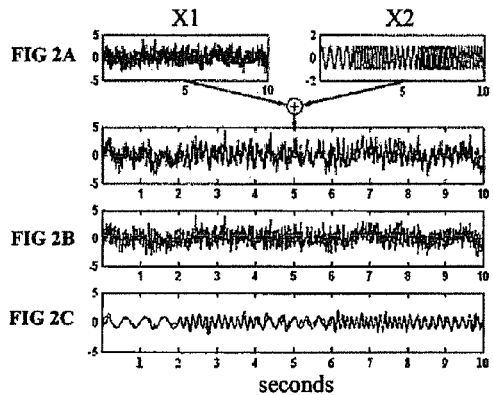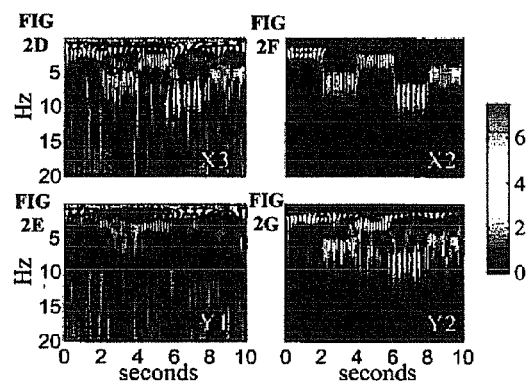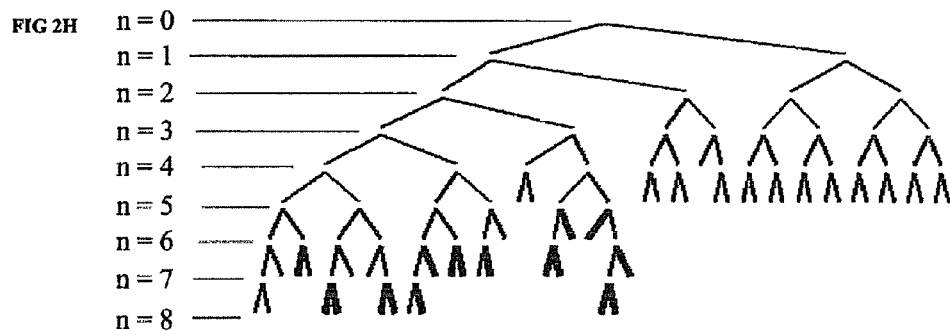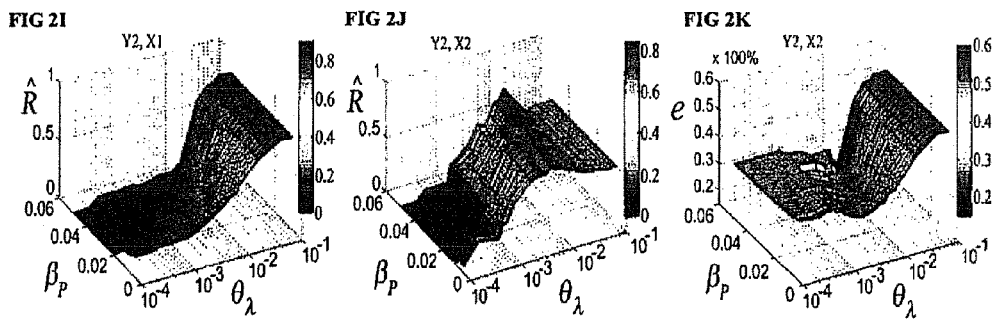

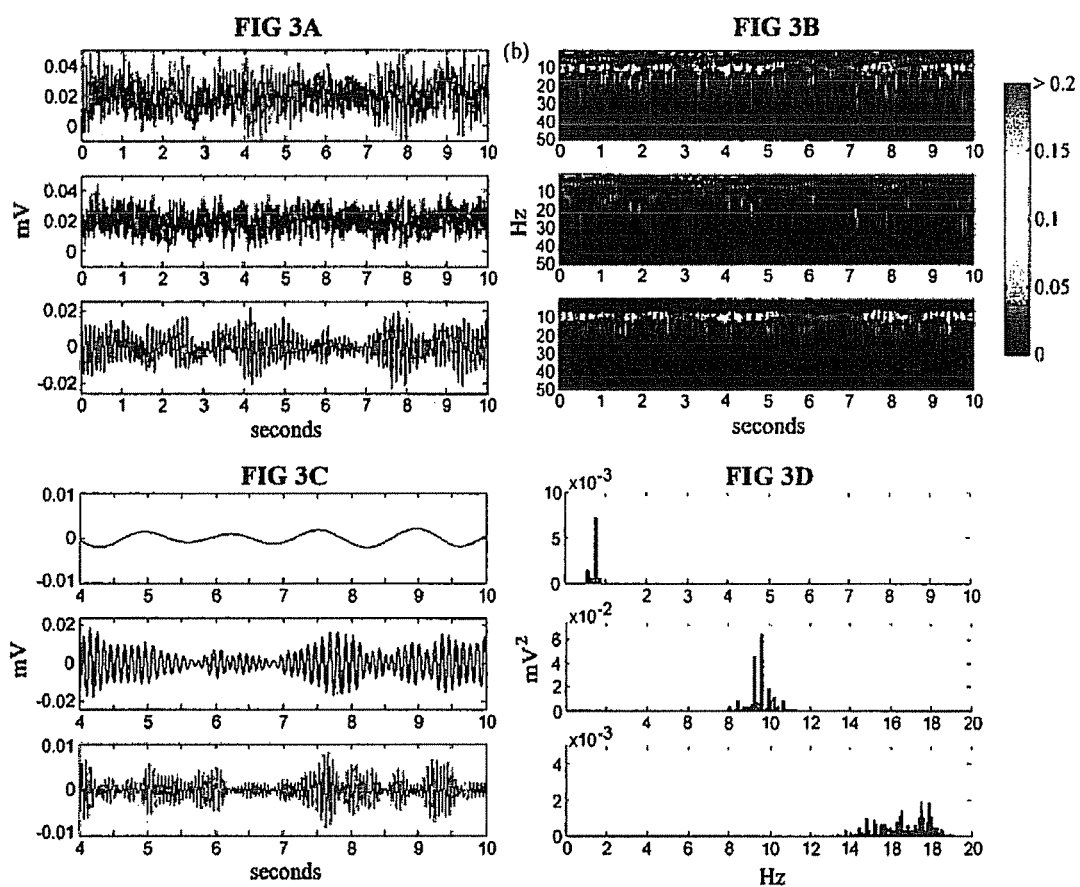

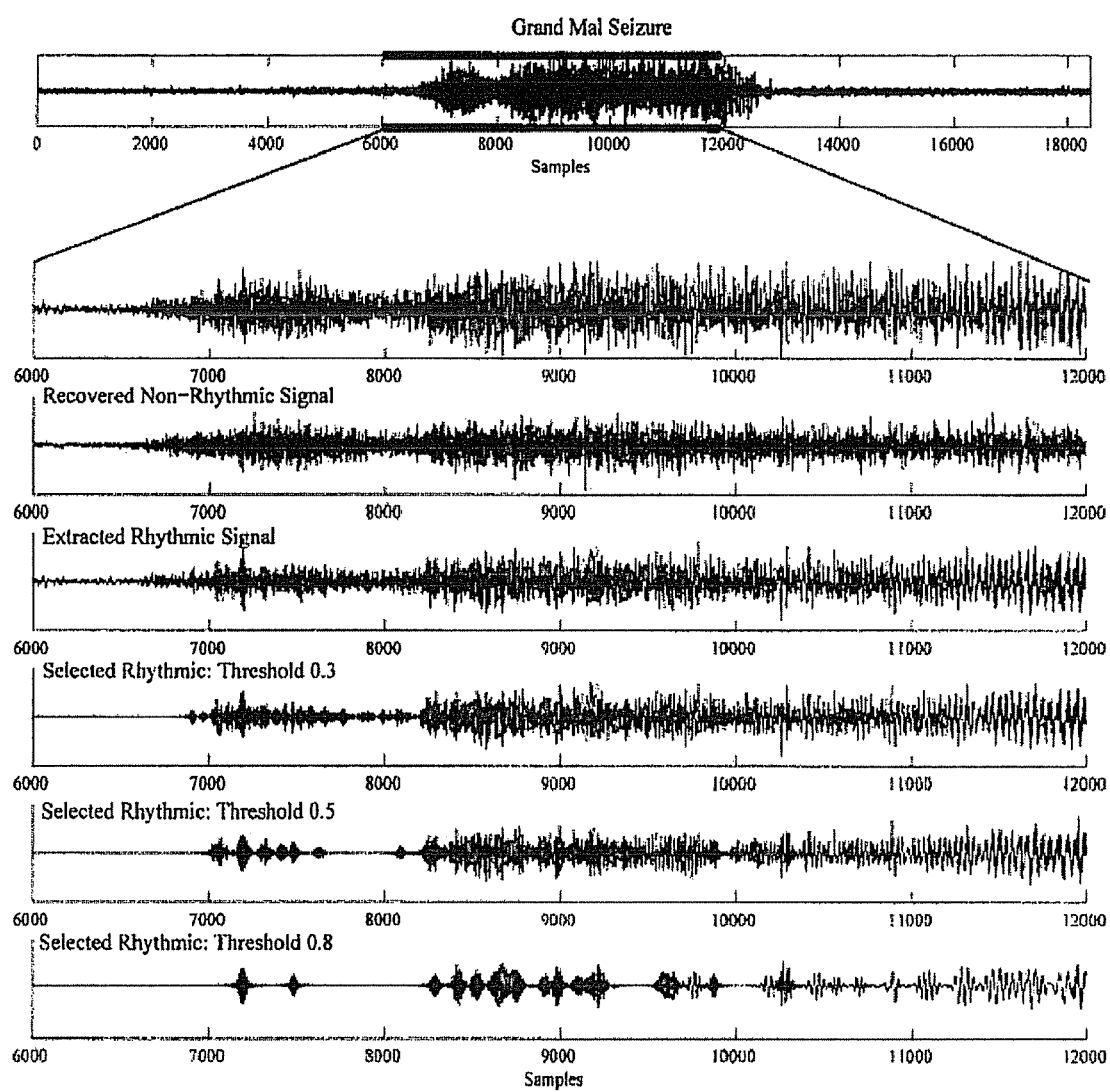

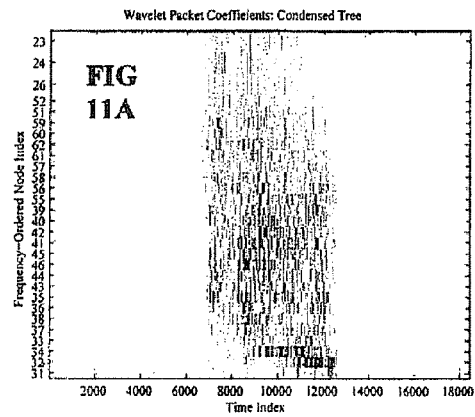
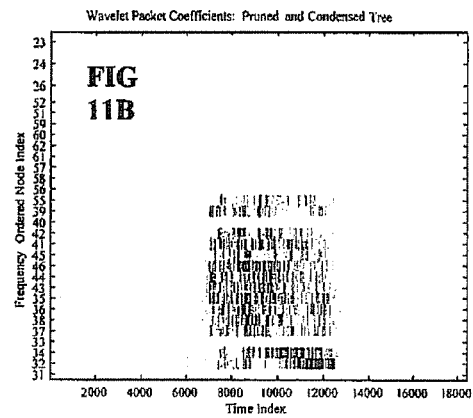
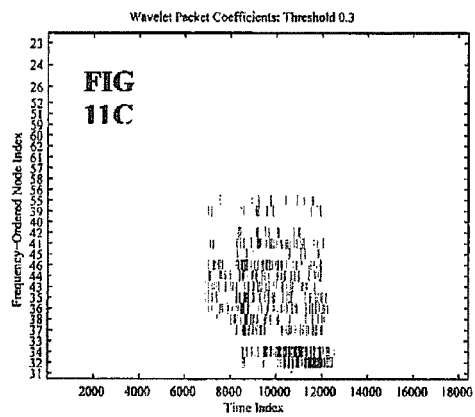
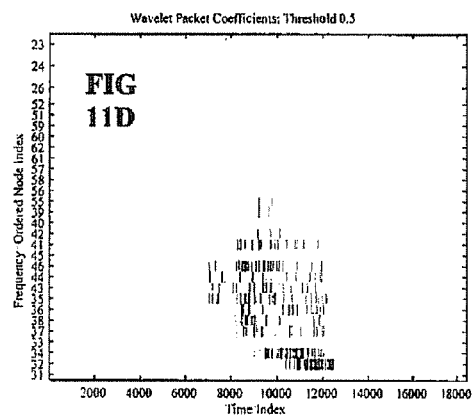
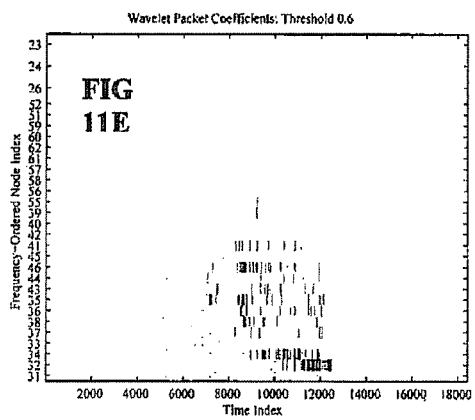
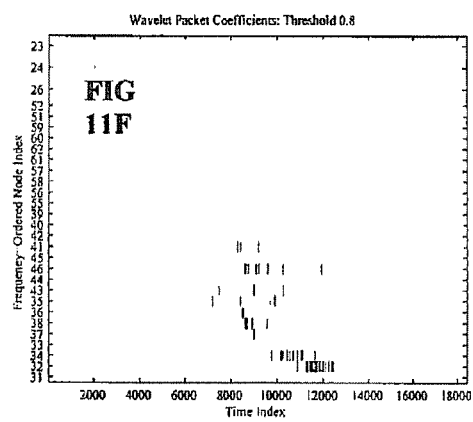

EEG signal can be separated into "more rhythmic components" and "less rhythmic components ("Noise")" then further broken down into frequency components.

Frequency Components

- With the guide of the power spectrum or the wavelet transform, either the more rhythmic or the less rhythmic components can further be decomposed into frequency components

- These frequency components are more effective in classifying brain states than the frequency components extracted straight from the total EEG

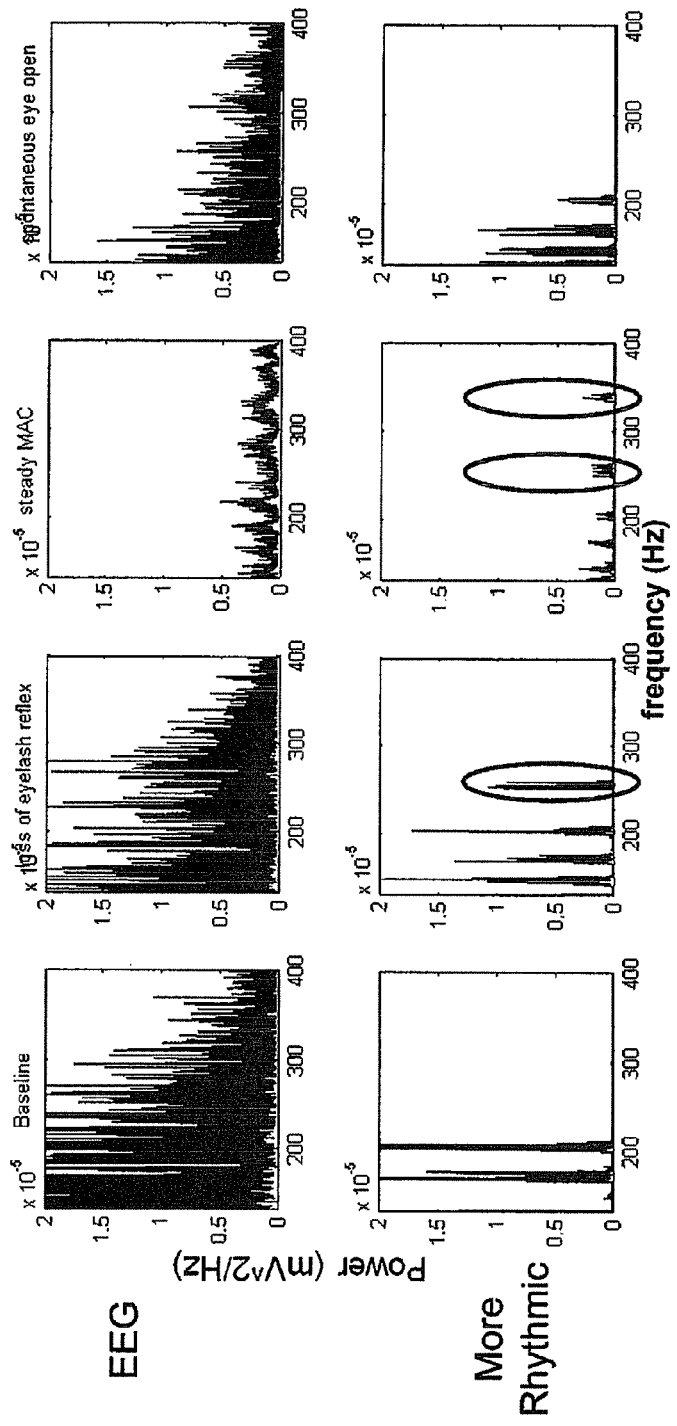
Fig. 17 Power Spectrum of the Extracted Components (High Frequency >50 Hz)
Distinct frequency rhythms emerge and disappear as the brain states change

METHOD AND RHYTHM EXTRACTOR FOR DETECTING AND ISOLATING RHYTHMIC SIGNAL FEATURES FROM AN INPUT SIGNAL USING THE WAVELET PACKET TRANSFORM

CROSS-REFERENCE TO RELATED APPLICATIONS

This application claims the benefit of U.S. Provisional Application No. 61/106,944 filed on Oct. 20, 2008 to Zalay entitled "Method for Detection and Extraction of Rhythms and Rhythmic Features from Discrete-Time Biological Signals Using the Wavelet Packet Transform", the content of which is incorporated herein by reference.

FIELD OF THE INVENTION

The present invention relates generally to signal processing and in particular to a method and rhythm extractor for detecting and isolating rhythmic signal features from an input signal.

BACKGROUND OF THE INVENTION

Rhythmic signals or rhythms are generated by various sources. Within the context of the following description, a rhythm, is defined as any modulation, fluctuation or recurrent pattern of activity within a signal or derivative thereof that has a measureable frequency or frequency range associated with it, and a duration of at least two or more cycles as defined by the time interval of recurrence, which itself may be variable over time.

Neural rhythms are associated with different brain functions and pathological conditions. The non-stationary nature of neural rhythms makes them difficult to detect and isolate. The intricate texture of neural recordings, which are interwoven with time-varying rhythmicities, nonlinearities, random fluctuations and artifacts, presents a considerable challenge for signal analysis. Observation of certain features may be crucial for clinical monitoring or diagnosis. For instance, the relative power and coherence of the delta, theta, alpha or gamma band rhythms can be related to different functional states of the brain. Other abnormal rhythmic features, such as high-frequency (>100 Hz) oscillations, have been implicated in neurological disorders such as epilepsy and Parkinson's disease. Therefore, robust separation of signal features based on rhythmicity is not only desirable but necessary.

Fourier transform methods are ill-suited to deal with non-stationary signals. As an alternative, the wavelet transform has proven itself to be versatile and effective, with improved ability to resolve signal features in both the time and frequency domains.

In the continuous wavelet transform, the input signal is convolved with a mother wavelet that is infinitely scalable and translatable. This generates an arbitrary wavelet basis for signal representation. The resulting analysis is computationally intensive with inherent redundancy in the wavelet coefficients, and exact reconstruction of the input signal is not possible for non-orthogonal bases. The discrete wavelet transform (DWT) eliminates redundancy by using an orthogonal or biorthogonal wavelet basis, usually with dyadic scaling and translation. The wavelet basis is used to formulate a finite impulse response quadrature mirror filter-bank for signal decomposition and reconstruction. The DWT therefore allows for multi-resolution analysis, which is superior to conventional filtering methods for isolating rhythms, because multi-resolution analysis subdivides and covers the time-frequency plane, whereas single-stage finite infinite response or infinite impulse response filters are limited in bandwidth and resolve frequencies but not temporal features. The discrete wavelet packet transform (DWPT or WPT) is an extension of the discrete wavelet transform (DWT) and enables greater frequency resolution of the input signal, especially at higher frequencies, where the resolution of the DWT is not as good.

The manner in which the time-frequency plane is subdivided by wavelet or wavelet packet transform-based multi-resolution analysis is dependent on the selection of the discrete wavelet or wavelet packet basis functions. The selection of the appropriate basis is related to the intended application of the analysis procedure.

Coefficient-thresholding basis selection methods have been developed for data compression and signal de-noising applications, including minimization of Stein's unbiased risk estimate (SURE), as discussed in the publication entitled "Adapting to unknown smoothness via wavelet shrinkage" authored by Donoho et al., *Journal of the American Statistical Association*, 90:1200-1224, 1995, and empirical Bayes estimates, as discussed in the publication entitled "Adaptive wavelet thresholding for image de-noising and compression" authored by Chang et al., *IEEE Transactions on Image Processing*, 9(9):1532-1546, 2000. However, such methods assume statistical properties of the observed data that cannot be intrinsically verified, but only estimated, including the nature and underlying distribution of the noise or wavelet coefficients. Also, the choice of wavelet basis functions and the order of decomposition are left to the user, and these can affect the performance of the estimators. Furthermore, none of the aforementioned techniques are specific to the task of detecting and isolating/extracting rhythmic features from a given input signal.

It is therefore an object of the present invention to provide a novel method and rhythm extractor for detecting and isolating rhythmic signal features from an input signal.

SUMMARY OF THE INVENTION

Accordingly, in one aspect there is provided A method of detecting and isolating at least one rhythmic signal component from a discrete-time input signal, comprising subjecting the input signal to discrete wavelet packet transform multi-resolution analysis, applying wavelet packet basis selection criteria to the result of the analysis, at each stage of the analysis, to evaluate the wavelet packet transform decomposed signal components of the input signal, detecting at least one rhythmic signal feature from the input signal based on the evaluation and isolating the detected at least one rhythmic signal feature from the input signal.

In one embodiment, the selection criteria are formulated to evaluate the degree of rhythmicity of signal components and the average power of the signal components. The wavelet packet transformation and selection criteria are applied recursively and the degree of rhythmicity of the signal components and the average power of the signal components are evaluated at each level of recursion. The degree of rhythmicity is based on interpeak interval variance.

The detected at least one rhythmic signal feature is processed to isolate individual rhythms or rhythmic components therein. During the processing, wavelet packet coefficients or coefficient nodes are pruned.

According to another aspect there is provided a method of isolating at least one rhythmic signal component from a discrete-time input signal comprising decomposing the input signal using the discrete wavelet packet transform to create a wavelet packet tree, pruning the wavelet packet tree and following pruning, selecting one or more coefficients or coefficient nodes of the wavelet packet tree containing rhythmic signal features thereby to isolate at least one rhythmic signal component of the input signal.

According to another aspect there is provided method of isolating rhythmic signal features of a discrete-time signal comprising subjecting the input signal to wavelet packet transforming and thresholding to evaluate the coefficients or coefficient nodes to be pruned with respect to rhythmicity and separating coefficients or coefficient nodes for independent preservation and time series reconstruction of rhythmic signal features.

According to yet another aspect there is provided a computer readable medium embodying computer readable code for detecting and isolating at least one rhythmic component from a discrete-time input signal, said computer readable code comprising program code for subjecting the input signal to discrete wavelet packet transform multi-resolution analysis, program code for applying wavelet packet basis selection criteria to the result of the analysis, at each stage of the analysis, to evaluate the wavelet packet decomposed signal components of the input signal, program code for detecting at least one rhythmic signal component based on the evaluation and program code for isolating the detected at least one rhythmic signal component from the input signal.

According to yet another aspect there is provided a computer readable medium embodying computer readable code for isolating at least one rhythmic signal component from a discrete-time input signal comprising program code for decomposing the input signal using the discrete wavelet packet transform to create a wavelet packet tree, program code for pruning the wavelet packet tree and program code for following pruning, selecting one or more coefficients or coefficient nodes of the wavelet packet tree containing rhythmic signal features thereby to isolate at least one rhythmic signal component of the input signal.

According to yet another aspect there is provided a computer readable medium embodying computer readable code for isolating rhythmic signal features of a discrete-time signal comprising program code for subjecting the input signal to wavelet packet transforming and thresholding to evaluate the coefficients or coefficient nodes to be pruned with respect to rhythmicity and program code for separating coefficients or coefficient nodes for independent preservation and time series reconstruction of rhythmic signal features.

According to still yet another aspect there is provided a rhythmic signal extractor for detecting and isolating at least one rhythmic signal component from a discrete-time input signal, comprising a discrete wavelet packet transform multi-resolution analyzer for analyzing the input signal and evaluating rhythmic signal features of the input signal and a signal component isolator for isolating at least one rhythmic signal component from the input signal based on the evaluation.

BRIEF DESCRIPTION OF THE DRAWINGS

Embodiments will now be described, by way of example only, with reference to the accompanying drawings in which:

FIG. 2A is an example of a test signal formed from a random sequence signal and a time-varying sinusoidal signal;

FIG. 2B is a reconstructed non-rhythmic signal resulting from processing of the test signal of FIG. 2A using the WPRE method of FIG. 1B;

FIG. 2C is a reconstructed rhythmic signal resulting from processing of the test signal of FIG. 2A using the WPRE method of FIG. 1B;

FIG. 2D is the continuous wavelet transform spectrogram of the test signal of FIG. 2A;

FIG. 2E is the continuous wavelet transform spectrogram of the reconstructed non-rhythmic signal of FIG. 2B;

FIG. 2F is the continuous wavelet transform spectrogram of the time-varying sinusoidal signal of FIG. 2A;

FIG. 2G is the continuous wavelet transform spectrogram of the reconstructed rhythmic signal of FIG. 2C;

FIG. 2H is the wavelet packet analysis tree generated by the WPRE method of FIG. 1B during processing of the test signal of FIG. 2A;

FIG. 2I is a map of the zero-lag correlation of a WPRE extracted rhythmic signal versus a reference arrhythmic signal for various values of WPRE parameters;

FIG. 2J is a map of the zero-lag correlation of a WPRE extracted rhythmic signal versus a reference rhythmic signal for various values of WPRE parameters;

FIG. 2K is a map of the relative error pertaining to a rhythmic reference signal versus a WPRE extracted rhythmic signal;

FIG. 3A shows an exemplary signal from a human scalp EEG, the non-rhythmic EEG signal recovered using the wavelet packet rhythm extraction method of FIG. 1B, and the time series reconstruction of the extracted signal components;

FIG. 3B are the continuous wavelet transform spectrograms of the signals shown in FIG. 3A;

FIG. 3C are the individual frequency localized EEG band rhythms reconstructed from pruned nodes of the signals of FIG. 3A;

FIG. 3D shows Fourier spectra of the localized EEG band rhythms of FIG. 3C;

FIG. 9 show an exemplary human Grand Mal seizure EEG signal and the various results of applying the WPRE method and coefficient-threshold fine pruning to the EEG signal;

FIG. 11A is a depiction of the time-frequency distribution of the condensed wavelet packet coefficients before pruning;

FIG. 11B is a depiction of the time-frequency distribution of the condensed wavelet packet coefficients after applying the WPRE method and coarse pruning;

FIG. 11C is a depiction of the time-frequency distribution of the condensed WPRE wavelet packet coefficients after fine pruning with a threshold parameter of 0.3;

FIG. 11D is a depiction of the time-frequency distribution of the condensed WPRE wavelet packet coefficients after fine pruning with a threshold parameter of 0.5;

FIG. 11E is a depiction of the time-frequency distribution of the condensed WPRE wavelet packet coefficients after fine pruning with a threshold parameter of 0.6;

FIG. 11F is a depiction of the time-frequency distribution of the condensed WPRE wavelet packet coefficients after fine pruning with a threshold parameter of 0.8;

FIG. 17 shows the power spectra of extracted higher frequency rhythmic signal components;

DETAILED DESCRIPTION OF THE PREFERRED EMBODIMENTS

In the following, a wavelet packet rhythm extraction (WPRE) method and rhythm extractor for carrying out the method is described that makes use of the discrete wavelet packet transform (DWPT) together with a threshold-based technique to automatically detect and isolate rhythmic signal features from input signals such as for example neural signal recordings. These isolated rhythmic signal features may then be independently reconstructed or combined into contiguous rhythms. The intended objective of the WPRE method therefore, is to extract and enable separation of rhythmic signal features so that they can be used in other signal processing-related applications such as detection, classification and tracking. The WPRE method is versatile because it can be applied to any input signal recorded from any source, whether it be an intracellular single-neuron recording or a recording of the integrated field-potentials of multiple neuronal populations.

Figure 1A:
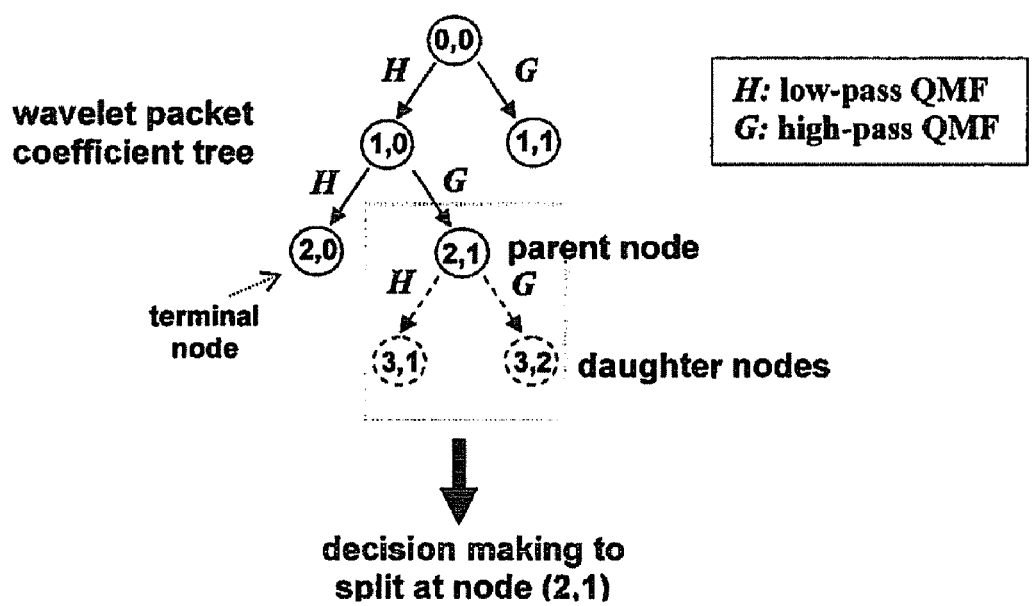
FIG. 1A is a schematic representation of a wavelet packet coefficient tree, generated by recursive application of basis selection criteria and wavelet packet transform.
Figure 1B:
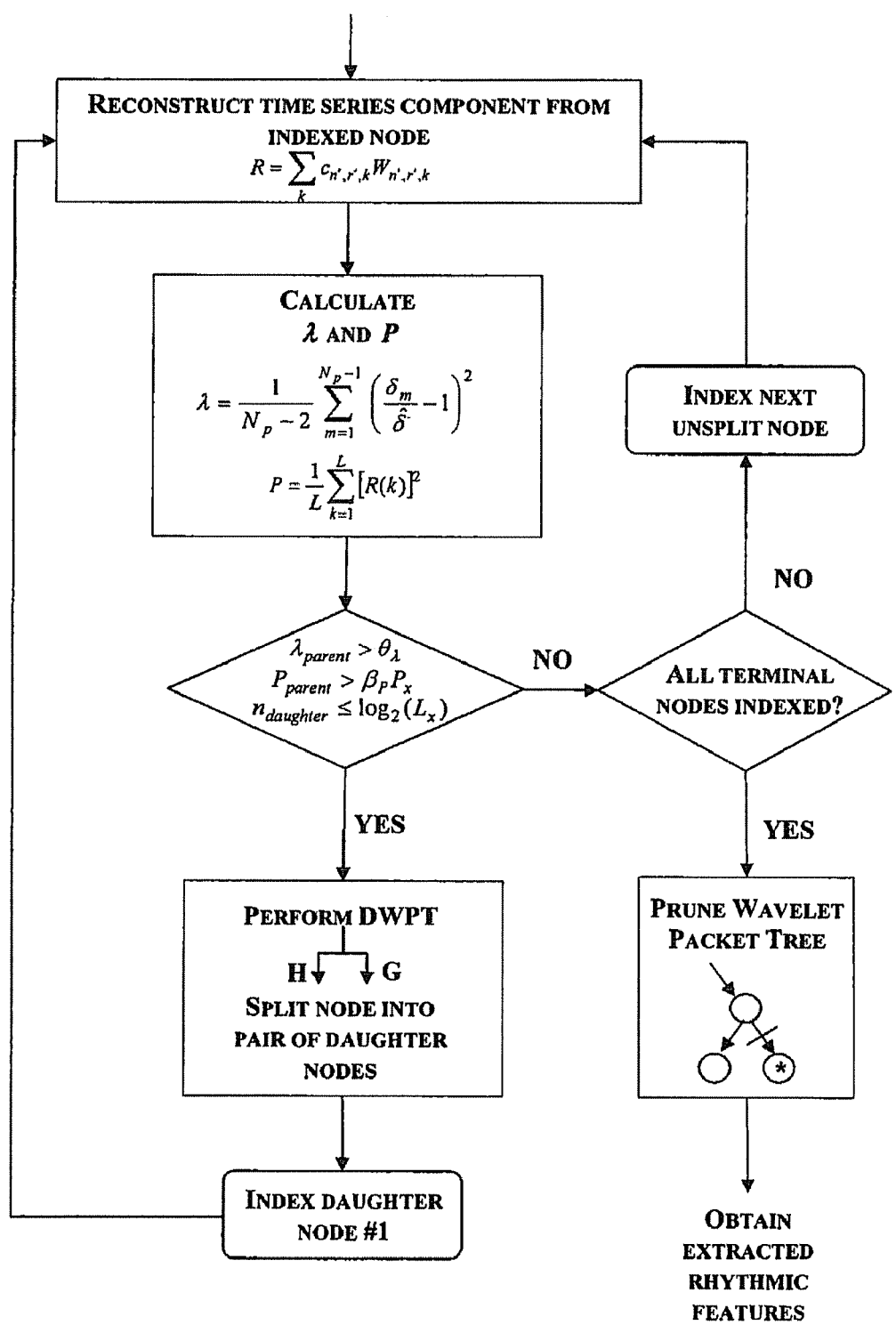
FIG. 1B is a flowchart of a wavelet packet rhythm extraction (WPRE) method.

Turning now to FIGS. 1A and 1B, the operation of wavelet packet node splitting and basis selection is shown. For a sampled signal of length $L=2^N$, analysis of the signal using wavelet packets generates a binary tree with a maximum depth of N levels. This results in a possible $(2^{N+1}-1)$ total number of coefficient nodes. For many applications, full binary tree decomposition is not required. Depending on the desired application, a reduced wavelet packet tree can be generated, either through selective pruning of tree nodes or by placing conditions on node splitting. The most commonly used optimization scheme is information cost minimization. During this scheme, an appropriate cost function (e.g. Shannon entropy) is used to gauge the information content of coefficients of the signal for a given orthonormal basis. The wavelet packet basis that generates the lowest information cost is selected. This approach is particularly suited to image and compression applications because of the efficiency in data representation.

To isolate rhythmic components or features from a signal, a metric based on the variance of peak-to-peak intervals in a given time series is defined. In this embodiment, the metric is the Normalized Interpeak Interval Variance (NIIV) and is expressed by:

$$\lambda = \frac{1}{N_P - 2} \sum_{m=1}^{N_P-1} \left(\frac{\delta_m}{\hat{\delta}} - 1\right)^2$$

where $N_P$ is the number of identified peaks (local maxima), $\delta_m$ is the mth interpeak interval, and $\hat{\delta}$ is the mean interpeak interval. As defined, NIIV $\lambda$ is a measure of the temporal variability of a time series. The more regular the signal, the lower the value of $\lambda$.

For example, a pure sinusoid has $\lambda=0$, since $\delta_m=\hat{\delta}$ for all m. Conversely, a signal with uniformly distributed random interpeak intervals has $\lambda=\frac{1}{3}$ (in the limit of infinite signal length). Normalization by $\hat{\delta}$ ensures the value of $\lambda$ is independent on the periodicity of the signal.

When implemented in the context of wavelet packet analysis, Normalized Interpeak Interval Variance provides a means of evaluating which coefficient nodes to prune with respect to the rhythmicity of their reconstructed time series. In this way, decomposed signal components can automatically be extracted should they fall below a set threshold value for $\lambda$. To avoid errors caused by spurious peaks, a small-window moving average filter (e.g. 3 samples) may be applied to smooth the time series prior to calculation. Also, constraints on which peaks are to be included in the determination of $\lambda$ may be introduced if necessary. For example, one such constraint might dictate that only peaks whose magnitude exceeds fraction $\chi$ of the mean peak size are to be included in the calculation.

To automate wavelet packet analysis, conditions for node-splitting are defined with respect to both $\lambda$ and average signal power of a given nodal time series reconstructed from its coefficients. The latter condition ensures the wavelet packet tree decomposition is not excessively thorough, in that as the original signal is decomposed into finer components, node splitting ceases at a particular node if its contribution to the cumulative power of the signal is insignificant.

For an arbitrary time series, s(k), of length L, the expression defining its average power is given by:

$$P = \frac{1}{L}\sum_{k=1}^{L}[s(k)]^2.$$

Let $\theta_\lambda$ be the threshold value for $\lambda$ and $0 \leq \beta_p < 1$ be the power significance level. If the splitting of one (parent) node into two daughter nodes is examined, then the following three conditions must hold for the splitting to be accepted:

$$\lambda_{parent} > \theta_\lambda$$

$$P_{parent} < \beta_P P_x$$

$$n_{daughter} \leq \log_2(L_x)$$

where $P_x$ is the average power of the starting signal, $L_x$ is its length, and n=0, 1, 2, ..., is the node level index. Practically, the power significance level $\beta_P$ controls the size of the resultant wavelet packet tree by controlling the depth of the analysis, up to the maximum level defined by $\max\{n_{daughter}\}$.

Once the node splitting process is complete and the resultant wavelet packet tree has been created, a pruning operation isolates the tree leaves (terminal nodes) that are below the threshold value $\theta_\lambda$. If desired, a different threshold value for pruning may be selected depending on the information that is required from the original signal. Since the wavelet packet tree preserves all information about the original signal, pruned nodes containing rhythmic signal components can be retained and independently reconstructed, thereby allowing for their isolated rhythmic features to be utilized in other applications.

The WPRE wavelet packet basis selection process relies on two parameters: the Normalized Interpeak Interval Variance threshold value $\theta_\lambda$, which pertains to defined in the Normalized Interpeak Interval Variance A and the power significance level $\beta_P$. Two values of $\theta_\lambda$ may be assigned: one for the analysis stage, to guide wavelet packet tree formation; and the other for the pruning stage, to select which terminal tree nodes containing rhythmic features are to be extracted. Different parameter values offer varying degrees of signal decomposition and filtering. Decompositions may be shallow or deep, depending on the required application. The power significance level $\beta_P$ controls the relative depth of the wavelet packet tree, though the maximum depth is determined by the total length of the time series as constrained by multi-resolution analysis. Therefore, the sampling rate is important, since a higher sampling rate for a recorded signal of the same time duration will yield a longer time series, and hence allow for a deeper wavelet packet tree analysis. This is a consequence of Nyquist's sampling theorem.

Shallow decompositions allow for isolation of rhythmic signal features with dominant spectral power, while deeper decompositions enable extraction of both dominant and weaker rhythmic signal features. Extraction of low-power, low-amplitude rhythmic signal features is possible even if their presence in a time series is not discernable by the eye, or by Fourier spectral analysis. This is important because experimental evidence shows brain oscillations exhibit an inverse relationship in signal power with increasing frequency. With EEG rhythms, higher frequency rhythms (e.g. beta and gamma) tend to be weaker in power compared to other more prominent low frequency rhythms (e.g. alpha or theta). Fourier methods for detecting or isolating rhythmic signal features are insufficient because of the manner in which the spectral power is averaged over time, thereby smoothing over and masking the time-dependent variation of rhythmic signal features. In contrast, the coefficients of the wavelet transform capture the temporal variation in the frequency composition of the signal.

As the power significance level $\beta_P$ is decreased, the threshold value $\theta_\lambda$ should be proportionally decreased as well. This is evident from the maps of FIGS. 2I to 2K, which show a slight shift in the best suited ridge for extraction of the time-varying rhythmic signal feature (highest correlation with sinusoidal reference, lowest error) towards lower threshold values $\theta_\lambda$ for smaller power significance levels $\beta_P$. The reason has to do with the narrowing of the frequency sub-bands analyzed by wavelet packet nodes at a given level, as wavelet packet tree depth increases. This implies, however, that choosing too small a value of the power significance level $\beta_P$ may lead to less than desired results, since the more rhythmic components of noise may also be extracted out. From empirical observation of the performance of the WPRE method on different signals using different parameters, a rule of thumb for the selection of the threshold for pruning is that the threshold value $\theta_\lambda$ should be roughly one order of magnitude smaller than the value of the power significance level $\beta_P$, as suggested by the location of the best suited ridge for extraction in the maps of FIGS. 2I to 2K. A threshold value $\theta_\lambda$ in the range of $10^{-3}$ to $10^{-2}$ was found to be appropriate for most signals, which makes sense because of the natural benchmarks on the interpeak interval variance measure ($\lambda$=0 for a pure sinusoid; $\lambda$=⅓ for a signal with uniformly distributed random interpeak intervals). An assessment of the efficacy of separation, however, is guided in practice by inspection of the continuous wavelet transform spectrogram of the output signals, or by examining the distribution of frequency-ordered wavelet packet coefficients in the time-frequency plane, in order to identify which rhythmic signal features have been successfully extracted.

A semi-empirical, data-driven technique for selecting appropriate analysis parameters is employed, and involves first performing a coarse decomposition of the signal, using a discrete wavelet transform (DWT), to the maximum depth allowed, and measuring $\lambda_i$ and $P_i$ for the ith detail signal originating from the wavelet coefficient time series. The DWT is a special sub-case of the discrete wavelet packet transform (DWPT), as the wavelet packet tree can be collapsed into an equivalent wavelet tree. The measured values of each reconstructed time series pertaining to the DWT coefficients can then be used to estimate the approximate $\theta_\lambda$ and $\beta_P$ parameters for wavelet packet rhythm extraction. If $P_x$ is the average power of the input signal, then:

$$\beta \sim \frac{1}{N} \sum_i^N \frac{P_i}{P_x}$$

is assumed to be an overestimate of $\beta_P$ since DWT is a coarser decomposition and DWPT is a finer decomposition. Likewise an assumed overestimate of $\theta_\lambda$ is derived from the weighted $\lambda_i$:

$$\theta \sim \frac{1}{P_x} \sum_i^N P_i \lambda_i$$

Since $\beta$ and $\theta$ are considered overestimates, scale factors dependent on N, the decomposition order, can be introduced to produce reasonable estimates $\hat{\theta}_\lambda$ and $\hat{\beta}_P$ of the $\theta_\lambda$ and $\beta_P$ parameters according to:

$$\hat{\theta}_\lambda \sim \frac{\theta}{k_\theta \log_2(N)}$$

$$\hat{\beta}_P \sim \frac{\beta}{k_{\hat{\beta}} \log_2(N)}$$

wherein, in this embodiment, k=½ and k=2. Nodes generated by the WPRE method can be ordered according to increasing frequency, and contiguous rhythms can be assembled from pruned nodes clustered together in the frequency domain. For a frequency-ordered wavelet packet tree with level index n=0, 1, 2, ..., N, frequency index v=0, 1, ..., $2^n-1$, and time series sampling period $\Delta t$, the sub-band localization of coefficient nodes approximately follows:

$$f_{n,v} \sim \frac{v}{2^{n+1}\Delta t}$$

where the exact relationship depends on the frequency characteristics of the analyzing wavelet packet functions. To quickly assess the frequency contents and spread attributed to a given node, a fast Fourier transform (FFT) spectral analysis of its reconstructed time series is sufficient. Direct reconstruction of neural rhythmic signal features from pruned nodes is straightforward if there are no competing rhythmic artifacts, but if such artifacts are present, it may be difficult to separate them out by inspection alone, due to their overlapping time-frequency features.

Independent component analysis (ICA) (Hyvarinen, A., and E. Oja. "Independent component analysis: algorithms and applications", Neural Netw. 13(4-5): 411-430, 2000) is one technique that can supplement the WPRE method to enable separation of rhythmic artifacts extracted together with genuine source rhythmic signal features. The premise of ICA for source separation assumes that the observed multivariate time series data $x=[x_1(t), x_2(t), \ldots, x_q(t)]^T$ are comprised of mixtures of independent sources, $s=[s_1(t), s_2(t), \ldots, s_m(t)]^T$, m≤q, which are not directly observable:

$$x=Ms$$

where M is an unknown q×m mixing matrix. Estimating s typically requires that x=Ms be linearly transformed:

$$\tilde{x}=Dx=DMs=As$$

so that the components of $\tilde{x}$ are reversibly whitened (i.e. de-correlated and normalized to have unit variance), and the dimensionality is reduced by principal component analysis (PCA) so that $\tilde{x}$ has the same dimensions as s. It is also prudent to assume the components of s have unit variance, since it is impossible to estimate their true variances. Consequently, A is an m×m orthogonal matrix that is easier to estimate than M, and its inverse is simply its transpose, hence:

$$s=A^T\tilde{x}=W\tilde{x}$$

The elements of the weights, W, are chosen so that the mutual information between m source signals of s is minimized, thereby maximizing their independence. This is equivalent to maximizing negative entropy, $J(\bullet)$, approximated by:

$$J(w_j) \sim (E(G(w_j\tilde{x}))-E(G(u)))^2$$

where $w_j$ is a 1×m row (weight) vector of W, $E(\bullet)$ is the expected value, u is a standardized Gaussian random sequence and $G(\bullet)$ is a nonlinear contrast function suitably chosen to discriminate between component $w_j\tilde{x}=s_j(t)$ and u. To generalize for multiple weight vectors, the optimization problem becomes the following:

$$W = [\hat{w}_1 \quad \hat{w}_2 \quad \ldots \quad \hat{w}_m]^T \text{ such that } \sum_{j=1}^{m} J(\hat{w}_j) = \max\left\{\sum_{j=1}^{m} J(w_j)\right\}$$

where appropriate constraints are prescribed to preserve the statistical independence of the sources, the orthogonality of W, and to ensure the boundedness of individual weight vectors so that the search space is sufficiently constrained.

Once s has been determined by ICA, sources that are clearly identified as artifacts (such as 60 Hz electrical noise) can be removed by setting those elements of s to zero, and the artifact-free observables can then be reconstituted using the equation for $\tilde{x}$, upon de-whitening A.

Figure 4:
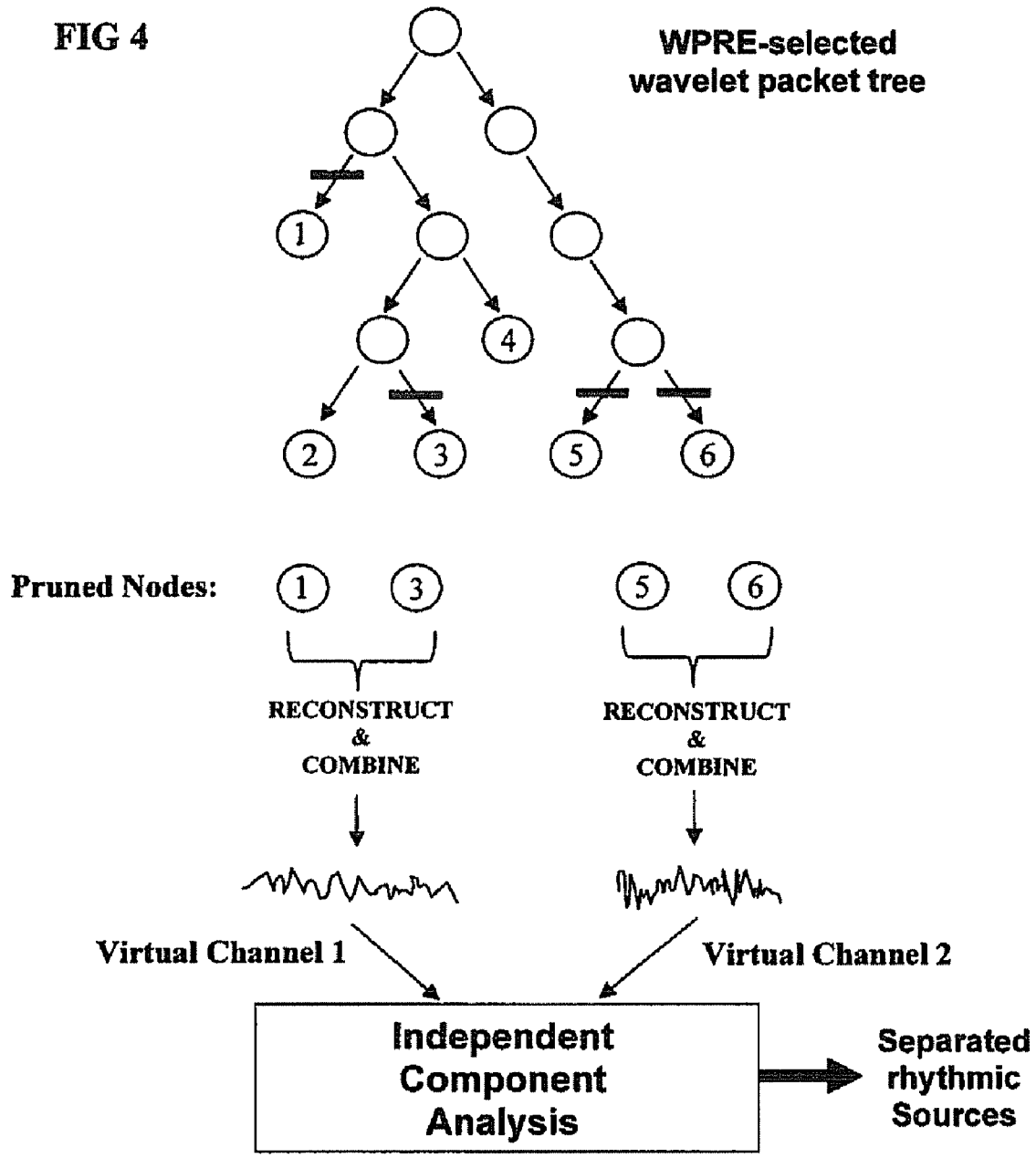
FIG. 4 shows an exemplary wavelet packet tree and the technique for creating virtual channels from its pruned nodes.

In practice, ICA requires that the multivariate time series x be obtained by simultaneously recording from q separate channels. However, with the WPRE method, there may be one signal to be analyzed that contains multiple rhythmic sources. Therefore, following WPRE wavelet packet filtering that selects for and isolates those rhythmic signal features, the pruned nodes containing the extracted rhythmic signal features can be used to construct virtual channels for ICA. This is accomplished by partitioning the pruned nodes (according to sequential or frequency order) and combining their nodal reconstructions into q time series as shown in FIG. 4. The WPRE method is beneficial as a preprocessing step to ICA, because it concentrates signal features and reduces noise, thereby facilitating source separation. More virtual channels can be constructed than are needed, and the dimensionality can be reduced through principal component analysis that precedes the optimization stage of ICA. Limitations to ICA include the arbitrary scaling and polarity of the independent components, and the need to assume or estimate the number of sources a priori.

Turning to the mathematical foundations of wavelet transforms, in general, for an N level multi-resolution analysis of a signal using the discrete wavelet transform (DWT), the signal is represented by the expression:

$$x(t) = A_N(t) + D_N(t) + \ldots + D_1(t)$$

$$= \sum_k c_k^{A,N} \phi_{N,k} + \sum_N \sum_k c_k^{D,n} \psi_{n,k}$$

where $A(t)$ and $D(t)$ are approximation and detail signals, $c_k^{A,n}$ and $c_k^{D,n}$ are the nth level approximation and detail coefficients, and $\phi_{n,k}$ and $\psi_{n,k}$ are the associated scaling and wavelet basis functions, respectively, having the form $$u_{j,k} = \sqrt{2^{-j}} u(2^{-j}t-k).$$

The scaling and wavelet functions are related by the two-scale expressions:

$$\phi(t) = \sqrt{2} \sum_k h_k \phi(2t-k)$$

$$\psi(t) = \sqrt{2} \sum_k g_k \phi(2t-k)$$

where h and g constitute finite quadrature-mirror filter (QMF) impulse responses selected/designed to provide the scaling and wavelet functions with specific time or frequency-domain properties. It is desired that the impulse responses are symmetric so that phase response is linear. The (n+1)-level approximation and detail coefficients are computed by discrete convolution of the previous nth level approximation coefficients with the time-reversed QMF coefficients, along with downsampling by 2:

$$c_k^{A,n+1} = [h_{-k} * c_k^{A,n}](\downarrow 2) = \sum_m h_{m-2k} c_m^{A,n}$$

$$c_k^{D,n+1} = [g_{-k} * c_k^{A,n}](\downarrow 2) = \sum_m g_{m-2k} c_m^{A,n}$$

To obtain a finer resolution analysis than the DWT, and for better discrimination of higher frequency features, the discrete wavelet packet transform (DWPT) is used. Implementation of the DWPT is similar to the DWT, except that the scaling and wavelet functions of the DWT are extended into a set of orthonormal wavelet packet functions, $W_m(t)$, which are defined by the recursion relations:

$$W_{2r}(t) = \sqrt{2} \sum_k h_k W_r(2t - k)$$

$$W_{2r+1}(t) = \sqrt{2} \sum_k g_k W_r(2t - k)$$

for integers $r \geq 0$, where $W_o(t) = \phi(t)$ and $W_1(t) = \psi(t)$. Multi-resolution analysis gives rise to a binary tree structure, with coefficient nodes generated from a dictionary of wavelet packet atoms having discrete scaling, translation and sub-band localization:

$$W_{n,r,k} = \sqrt{2^{-n}} W_r(2^{-n} t - k)$$

where the scale exponent $n = 0, 1, 2, \ldots$, corresponds directly to the level in the tree, and index $r = 0, 1, 2, \ldots, 2^n - 1$ corresponds to the horizontal node position. If tree nodes are re-ordered in terms of increasing frequency, then r becomes a frequency index relating to the sub-band analyzed by atoms $W_{n,r,k}$ at scale $2^n$ and time $2^n k$.

Signal decomposition via the DWPT is accomplished by sequentially splitting coefficient nodes into daughter node pairs, while synthesis involves the reverse operation. The leaves (terminal nodes) of the connected tree constitute an orthonormal basis from which the original signal can be represented by the following summation:

$$x(t) = \sum_{n'} \sum_{r'} x_{n',r'}(t)$$

where the reconstructed nodal time series:

$$x_{n',r'}(t) = \sum_k c_{n',r',k} W_{n',r',k}$$

are defined for (n', r') belonging to the set denoting the leaves of the tree (with coefficients $c_{n',r',k}$). The individual coefficients can themselves be used to generate feature sets following the WPRE method using clustering or thresholding techniques.

The operation of pruning of the resultant wavelet analysis tree, as it pertains to coefficients or coefficient nodes, is therefore the act of selecting one or more terminal coefficients or coefficient nodes, based on thresholding or other selection criteria, so as to separate them from the other coefficients in the tree, for purposes of their independent preservation and for time series reconstruction. The operation of time series reconstruction is also equivalent to setting non-selected coefficients in the tree to zero and performing the inverse DWPT using reconstruction filters to arrive at a zeroth-level approximation signal representing the basis defined only by the selected coefficients and their corresponding wavelet packet atoms.

The following is an exemplary application of the WPRE method to a test signal created by combining a normally-distributed random sequence, X1, with a time-varying sinusoid, X2 as shown in FIG. 2. The shifting frequency-time characteristics of sinusoid X2 and its spectral overlap with random sequence X1 make clean separation of the two signals from the test signal difficult. Various combinations of the Normalized Interpeak Interval Variance threshold $\theta_\lambda$ and power significance level $\beta_P$ are explored to achieve reasonable separation. In this example, the wavelet packet filtered signal is compared against random sequence X1, while the time series reconstruction of the pruned nodes containing the extracted rhythmic components is compared against sinusoid X2. Continuous wavelet transforms of the reconstructed signals visually indicate separation of the signals in the time-frequency plane; the filtered signal (Y1) is similar to random sequence X1, while the extracted signal (Y2) is similar to sinusoid X2. Color maps (FIGS. 2I to 2K) of the correlation coefficient and percentage root mean squared error illustrate a suitable ridge for signal separation for a pruning threshold between $10^{-3}$ to $10^{-2}$, corresponding to the power significance in the range of an order of magnitude larger. Along the ridge, both the error and the correlation of the extracted signal to random sequence X1 are minimized, and the correlation of the extracted signal to sinusoid X2 is maximized. As the pruning level becomes too high, eventually all components are isolated and extracted out, including arrhythmic or noisy components, which explains the surge in the correlation to random sequence X1 as $\theta_\lambda$ surpasses $\sim 2 \times 10^{-2}$, and why the correlation to sinusoid X2 drops off. Conversely, as $\theta_\lambda$ becomes too small, the constraint on what is considered rhythmic tightens to the extent that only some or none of the rhythmic signal components are isolated. Furthermore, there is a shift of the ridge toward lower $\theta_\lambda$ threshold values as the power significance level $\beta_P$ decreases since the power significance level $\beta_P$ controls the depth of the wavelet packet tree decomposition. As tree depth increases, there is a narrowing of the frequency sub-bands analyzed by wavelet packet nodes at each consecutive level, which means the node contents are more rhythmically pure; hence a lower pruning threshold is needed to compensate.

Figure 5A:
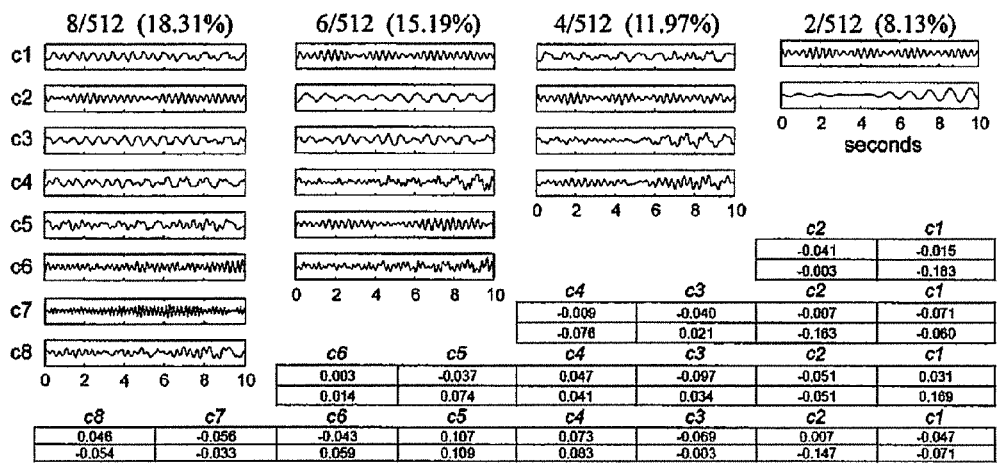
FIGS. 5A and 5B are examples of signal separation using straight wavelet packet decomposition and independent component analysis applied to the test signal of FIG. 2A.
Figure 5B:
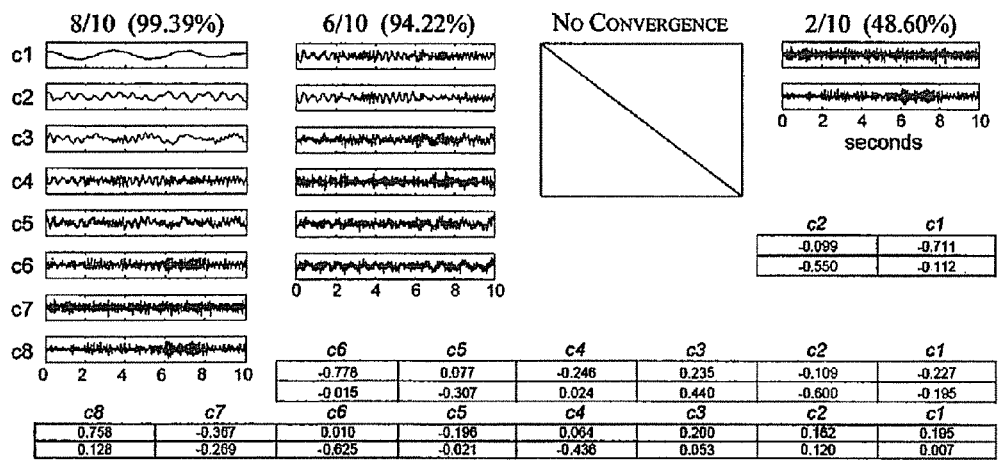

As a comparison, signal separation of the test signal of FIG. 2A composed of random sequence X1 and sinusoid X2 using independent component analysis (ICA) in combination with straight wavelet packet decomposition (without WPRE) is shown in FIGS. 5A and 5B. ICA requires multiple mixed channels as input, so reconstructed signals from wavelet packet node coefficients are used as input channels. A full wavelet packet tree of order 9 was generated (the maximum allowable size owing to physical memory constraints), with a total of 512 leaf nodes. In FIG. 5A, all 512 naturally-ordered nodes were used as input channels, while in FIG. 5B, the nodes are clustered according to their logarithmic frequency order into ten (10) virtual channels. Principal component analysis is used as a pre-processing step to ICA to reduce the data to a smaller number of components possessing the largest eigenvalues (and hence make the most contribution to explaining the variation in the test signal). This is done for separate trials using different numbers of components because the ideal number of components is not generally known.

To evaluate the trials, the correlation coefficients of each component with random sequence X1 and with sinusoid X2 are measured. The percentage error is not computed because the amplitude scaling and polarity of independent components is non-unique and dependent on the optimization process. If convergence is problematic, the trial is re-run using different randomized initialization values. Cubic and hyperbolic tangent derivative contrast functions are also utilized, and the function yielding the best convergence was selected for the final result.

As shown in FIG. 5A with all 512 channels, poor results are produced as the component correlations with both random sequence X1 and sinusoid X2 are low, meaning ICA does not capture enough of either signal. This indicates that using the raw output of wavelet packet decomposition as a precursor to ICA is not practical or reliable, since the percentage variance explained by the eight (8) or less dominant components in the trials is below 20% of that of the original signal. As shown in FIG. 5B, with nodes combined into frequency-ordered virtual channels, separation is much improved, as more than 90% of the signal variation could be captured by at least six to eight components. Correlation coefficient values for set 2 are also much higher, as a result of better separation. For example, in the 8-component trial, components c1, c3, c5 and c8 can be quantitatively identified as belonging principally to random sequence X1, whereas, components c6 and c4 belong to sinusoid X2, and c7 and c2 are still mixtures. This degree of separation approaches but does not surpass that of the WPRE method. The magnitude of the correlation is more important than the sign, as a negative sign implies inverted polarity of the component in relation to its originating signal. Convergence is not achieved for the 4-component trial, despite trying various initializations and exchanging contrast functions.

Figure 6:
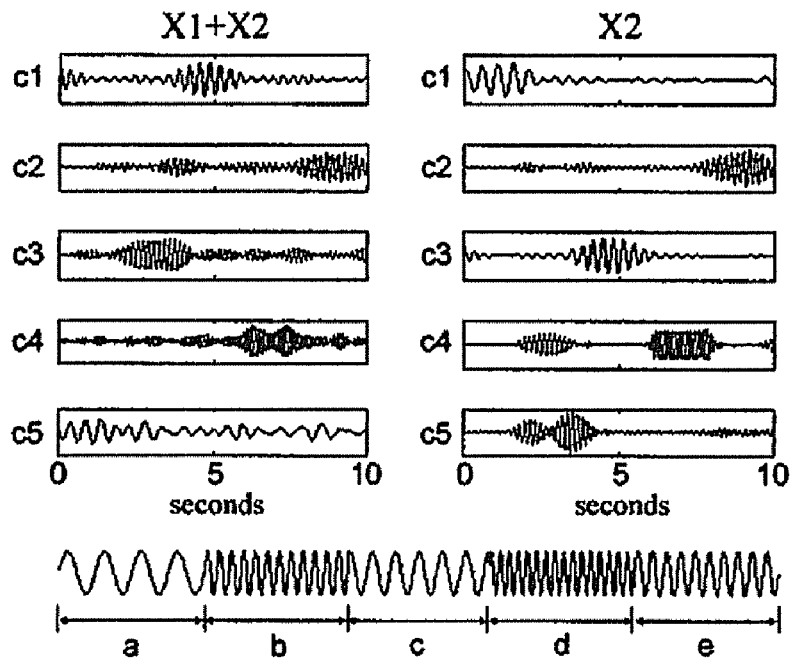
FIG. 6 is an example of rhythmic extraction following wavelet packet rhythm extraction techniques and independent component analysis applied to the test signal of FIG. 2A.

Taking advantage of the combination of ICA with wavelet packet analysis, if ICA is applied to either WPRE wavelet packet filtered or extracted signals, it may be possible to further discriminate sub-components within each group. Again, using the test signals of the previous examples, WPRE was applied followed by ICA on the pruned nodes, retaining >95% of the variation in five (5) components. FIG. 6 shows that separation of rhythmic subcomponents is feasible, and that each separated component can be correlated to its respective rhythmic segment in sinusoid X2, to within a sign. Separation of components for the noise-free signal is naturally superior to that of the combined signal, though the correlation with sinusoid X2 is not perfect because of the inherent spectral discontinuities in sinusoid X2 at the segment junctions. Also in the noise-free case, segment b is split between c4 and c5, as identified visually and by the correlation coefficient values.

Large amplitude spikes (LAS) are another common feature of biological signals, whether they are generated spontaneously or as a byproduct of stimulation. If LAS are associated with an underlying rhythm and require removal, then the WPRE method alone is not capable of eliminating all spike remnants, since spikes with large amplitudes in relation to the rest of the signal tend to dominate the coefficients of the wavelet (packet) transform across all frequency bands analyzed. Therefore, the signals should be "despiked" beforehand using an appropriate method that attenuates the spectrally dominant spike features, yet leaves the remainder of the signal intact. A suitable attenuation method is described in co-pending U.S. application Ser. No. 12/582,407 to Zalay filed on even date herewith and entitled "Method and System for Detection and Iterative Attenuation Of Spikes in Complex Signals", and assigned to Neurochip Corporation of Ontatrio, Canada, assignee of the subject application, the content of which is incorporated herein by reference. Therefore, in these cases, a spike attenuation stage should be implemented before using the WPRE method.

Secondly, if the signal is such that a particular frequency band or bands dominates over the others in terms of spectral power, a pre-processing technique to improve the sensitivity of the WPRE method in these circumstances should be employed. One such preprocessing technique involves (conventional) bandpass-filtering of the data into segments from low to high frequency, and performing parallel WPRE on each band-limited segment to extract the individual rhythms.

Figure 7A:
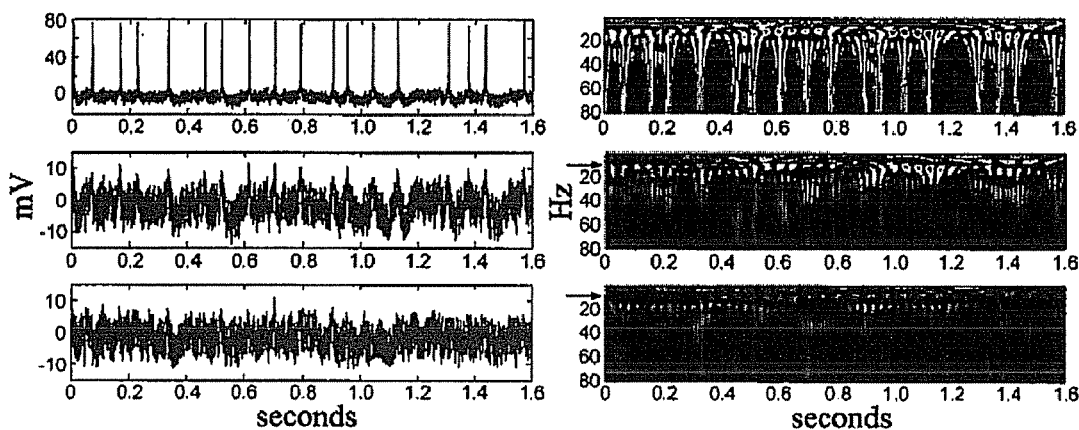
FIGS. 7A and 7B are examples of signal separation in the presence of large amplitude spikes.
Figure 7B:
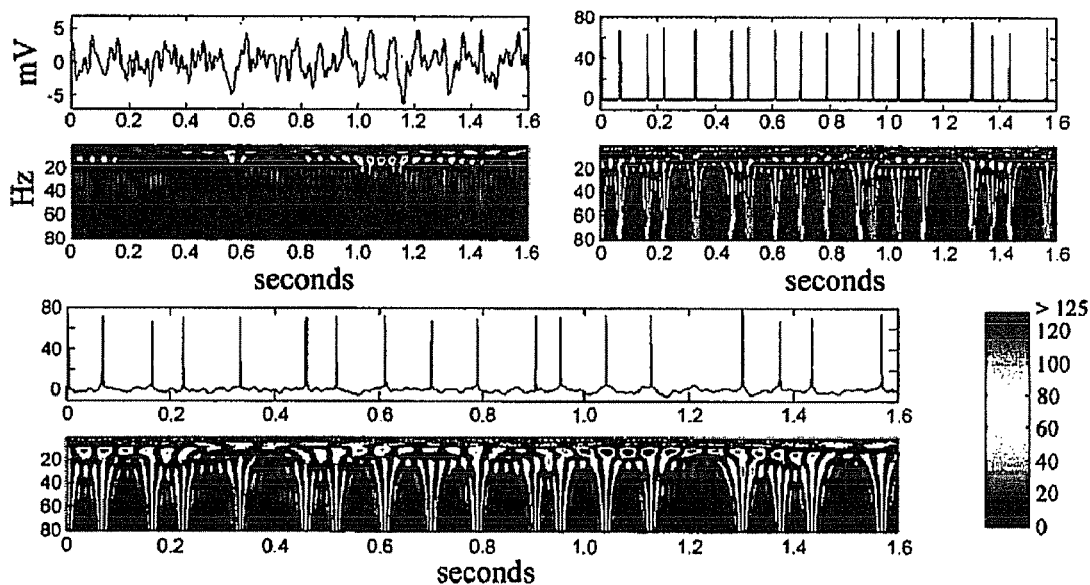

FIGS. 7A and 7B show an example of signal separation in the presence of large amplitude spikes. The WPRE method is applied to an intracellular recording of a hippocampal CA3 pyramidal neuron under low Mg2+ conditions exhibiting rhythmic spiking activity (in this example, on an in vitro rat hippocampal slice recording). As shown in FIG. 7A, the WPRE method successfully removes the action potentials and their underlying depolarizations following spike attenuation and wavelet packet filtering. The extracted rhythmic signal and spikes are shown in FIG. 7B, as well as their recombination to form a noise-reduced composite signal containing the restored action potentials as well as baseline depolarizations and sub-threshold rhythmic activity.

Extracellular field potentials reflect the summed activity of multiple neuronal populations in time and space. As such, electroencephalogram (EEG) recordings contain multiple embedded rhythms that originate from distributed source populations. Also, different rhythms predominate during different neurophysiological or pathophysiological states, which is an aspect that the EEG exploits as a diagnostic tool. EEG rhythms can be classified with reference to their frequency band localization, which by convention includes the delta (0.5-3.5 Hz), theta (3.5-7.5 Hz), alpha (7.5-12.5 Hz), beta (12.5-25 Hz), gamma (25-80 Hz) and super-gamma (>80 Hz) bands. The difficulties associated with analyzing EEG signals are often in detecting weaker rhythms masked by predominant ones and distinguishing which signal features pertain to which rhythms.

The raw EEG signal shown in FIG. 3A is from the occipital region, and exhibits a well-defined alpha rhythm. Upon analysis with the WPRE method, the time series is first decomposed into rhythmic and non-rhythmic signals, and the rhythmic signal is then further separated into three independent rhythms that are classified by Fourier spectral analysis as belonging to the delta, alpha and beta bands, respectively. These rhythms are reconstructed from pruned wavelet packet coefficient nodes grouped together according to their frequency position and order. The non-stationarity of the rhythms is evident in the spread of frequencies localized in each band. Without the WPRE method to isolate the three rhythms, the lower-power delta and beta rhythms may have been overlooked. The alpha power exceeds the gamma and delta power by an order of magnitude, and as a result, it is difficult to visually distinguish between the Fourier spectrum of the extracted signal versus the spectrum of the raw EEG signal.

Figure 8A:
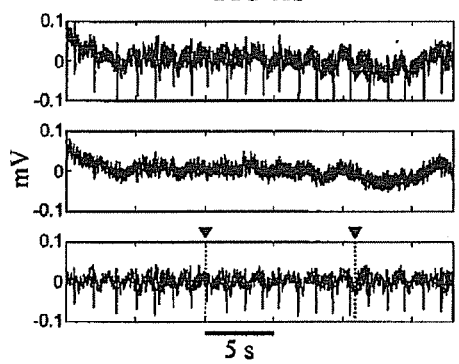
FIG. 8A shows exemplary raw EEG signals to which wavelet packet rhythm extraction is applied.
Figure 8B:
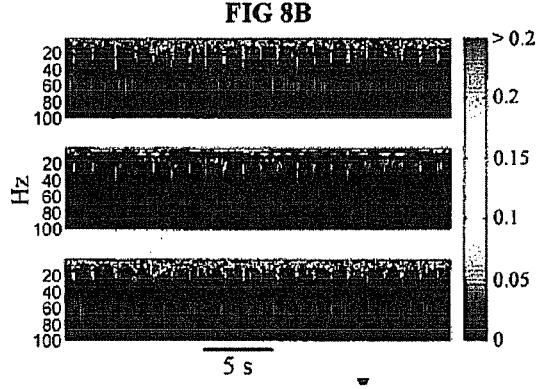
FIG. 8B are the continuous wavelet transform spectrograms of the raw EEG signals of FIG. 8A.

Scalp EEGs are prone to being contaminated by electrical noise, muscle artifacts and cardiac rhythms. An example of an artifact-contaminated EEG signal from the forehead is shown in FIG. 8A (top trace). The signal, which presents with prominent cardiac QRS spikes, is analyzed using the WPRE method and separated into non-rhythmic and rhythmic signal components (middle and bottom traces, respectively). Spike attenuation is not necessary before wavelet packet filtering because the spectral signature of the QRS complexes was fairly localized in frequency, and could therefore be removed with WPF as shown in FIG. 8B. A uniform band centered at 60 Hz attributed to alternating current electrical noise is also extracted.

Figure 8C:
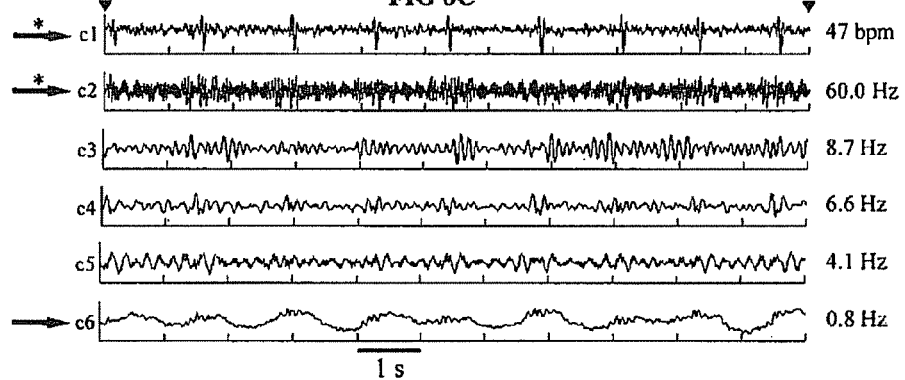
FIG. 8C are the estimated independent signal components from the extracted rhythmic signals of the raw EEG signals of FIG. 8A.
Figure 8D:
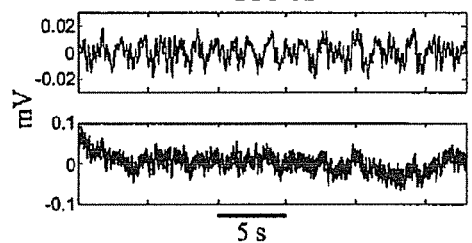
FIG. 8D are the reconstituted rhythmic signals following independent component analysis of the signals of FIG. 8A.
Figure 8E:
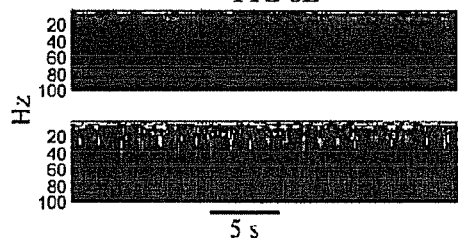
FIG. 8E are the continuous wavelet transform spectrograms of the reconstituted rhythmic signals of FIG. 8D.

Low-amplitude neural source rhythms in the range of 0-20 Hz, however, are masked by the spectrally dominant QRS complexes. These rhythms share the same time-frequency localization as the rhythmic QRS spikes; therefore, some of the pruned wavelet packet coefficient nodes contain a mixture of rhythmic artifact and genuine source features, and the WPRE method is unable to separate them further. Consequently, independent component analysis (ICA) is undertaken as an additional step to separate the extracted components based on the statistical differences between them, as is demonstrated in FIG. 6 on the test signal. From an initial pool of eight (8) virtual channels created from the frequency-ordered pruned nodes, six (6) sources are identified in FIG. 8C. Among the six components, c1 and c6 are likely cardiac in origin. Interspike interval analysis shows the QRS complexes in c1 have a mean frequency of 47 beats per minute (bpm) whereas Fourier analysis of c6 yields a spectral peak at 0.8 Hz, which translates to 48 bpm. Moreover, c1 and c6 are highly phase-correlated, which suggests a link between them. Fourier spectra of the other independent components are also computed. Component c2, which has a dominant peak at 60 Hz, and pertains to the 60 Hz A/C electrical artifact. Components c3 to c5 are putative neural source rhythms, with c3 situated in the alpha band (7.5-12.5 Hz), and c4 and c5 in the theta range (3.5-7.5 Hz). To demonstrate recovery of the observed signal following artifact removal, components c1 and c2 are eliminated and the observed signal reconstituted from the remaining independent components and the wavelet packet filtered signal is shown in FIG. 8D. FIG. 8E shows the continuous wavelet transform spectrogram of FIG. 8D.

For sparse representation of rhythmic features, or to enable greater temporal isolation of rhythmic components, a fine pruning of the wavelet packet analysis tree can be performed subsequent to Normalized Interpeak Interval Variance threshold pruning of coefficient nodes. This subsequent fine pruning involves setting or determining a magnitude threshold for wavelet packet coefficients, or otherwise applying a clustering or subspace method, such as C-means clustering or principal component analysis, in order to select individual coefficients from within each node of interest for time series reconstruction. The method is especially useful as a means of isolating short-duration rhythmic features that occur briefly in time within the larger signal, or for selecting the most prominent components of rhythmicity within contiguous rhythms.

Figure 10:
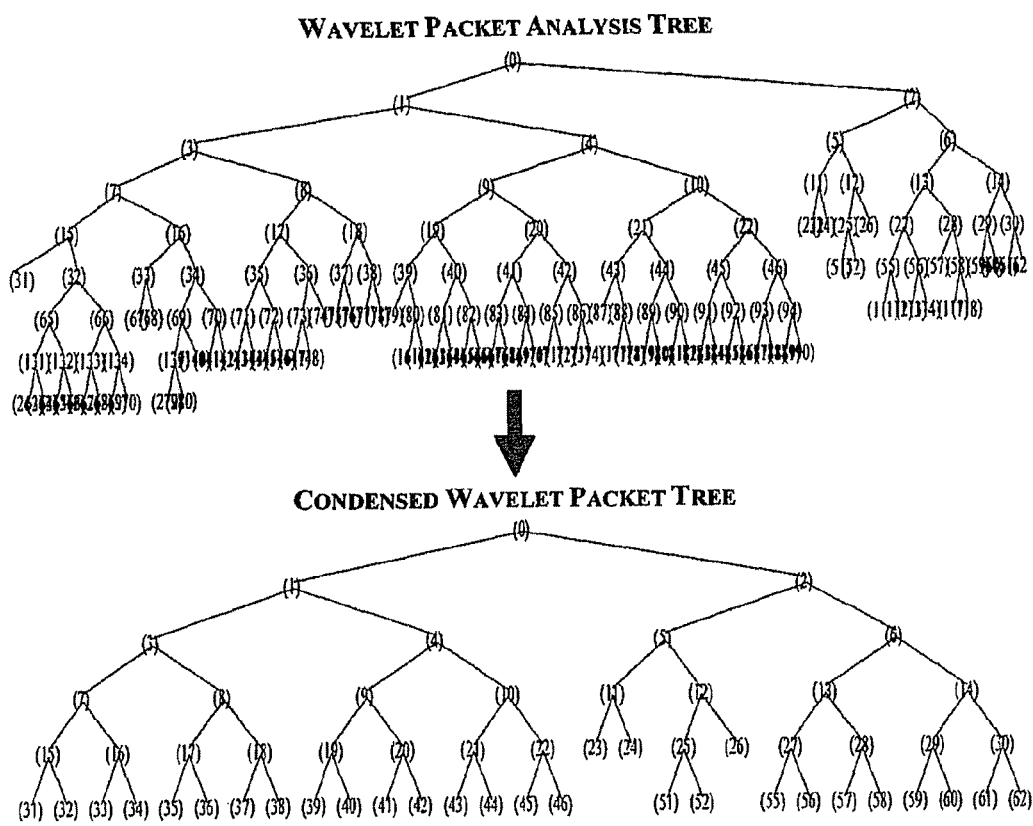
FIG. 10 is an exemplary wavelet packet analysis tree and its condensed format.

FIGS. 9 to 11 pertain to analysis of a recorded human Grand Mal seizure EEG signal using the wavelet packet rhythm extraction method, followed by a fine-pruning stage whereby coefficients from the extracted nodes containing rhythmic features are thresholded to select the most prominent coefficients by magnitude. In this exemplary embodiment of fine pruning, coefficients that fall below the threshold defined by $\eta$ are set to zero, $$\eta = \frac{\kappa}{N_c} \sum_{n \in T_c}^{N_c} \max_k \{|c_{[n],k}|\}$$

where the index n belongs to the subset $T_c$ of terminal coefficient nodes numbering $N_c$, selected by coarse pruning based on the Normalized Interpeak Interval Variance, and $\kappa$ is a user-defined threshold constant between 0 and 1. In alternative embodiments, the fine-pruning threshold for wavelet packet coefficients may be selected by adaptive methods that minimize a risk function associated with the assumed model and threshold, such as those described by Donoho et al. in the *Journal of the American Statistical Association*, 90:1200-1224, 1995, and in the article authored by Chang et al., *IEEE Transactions on Image Processing*, 9(9):1532-1546, 2000.

Figure 12:
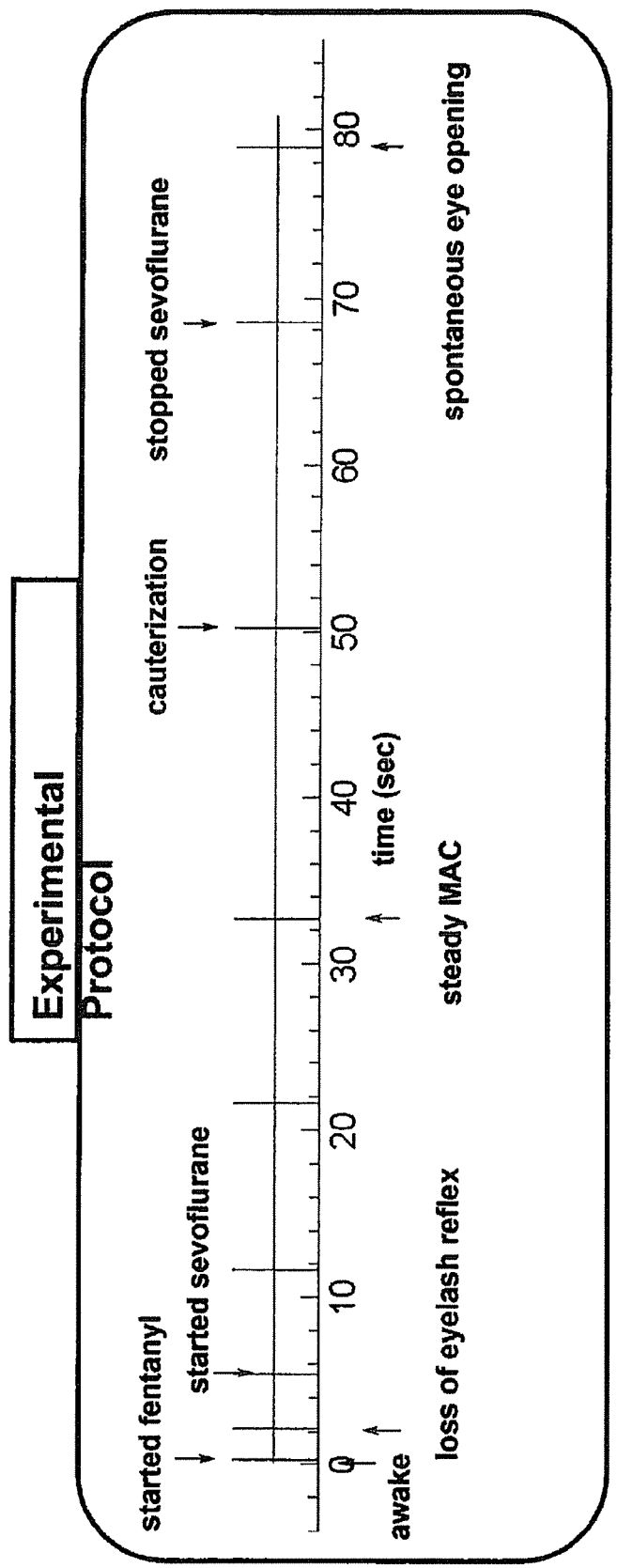
FIG. 12 shows a surgical protocol on six (6) patients undergoing surgery.
Figure 13:
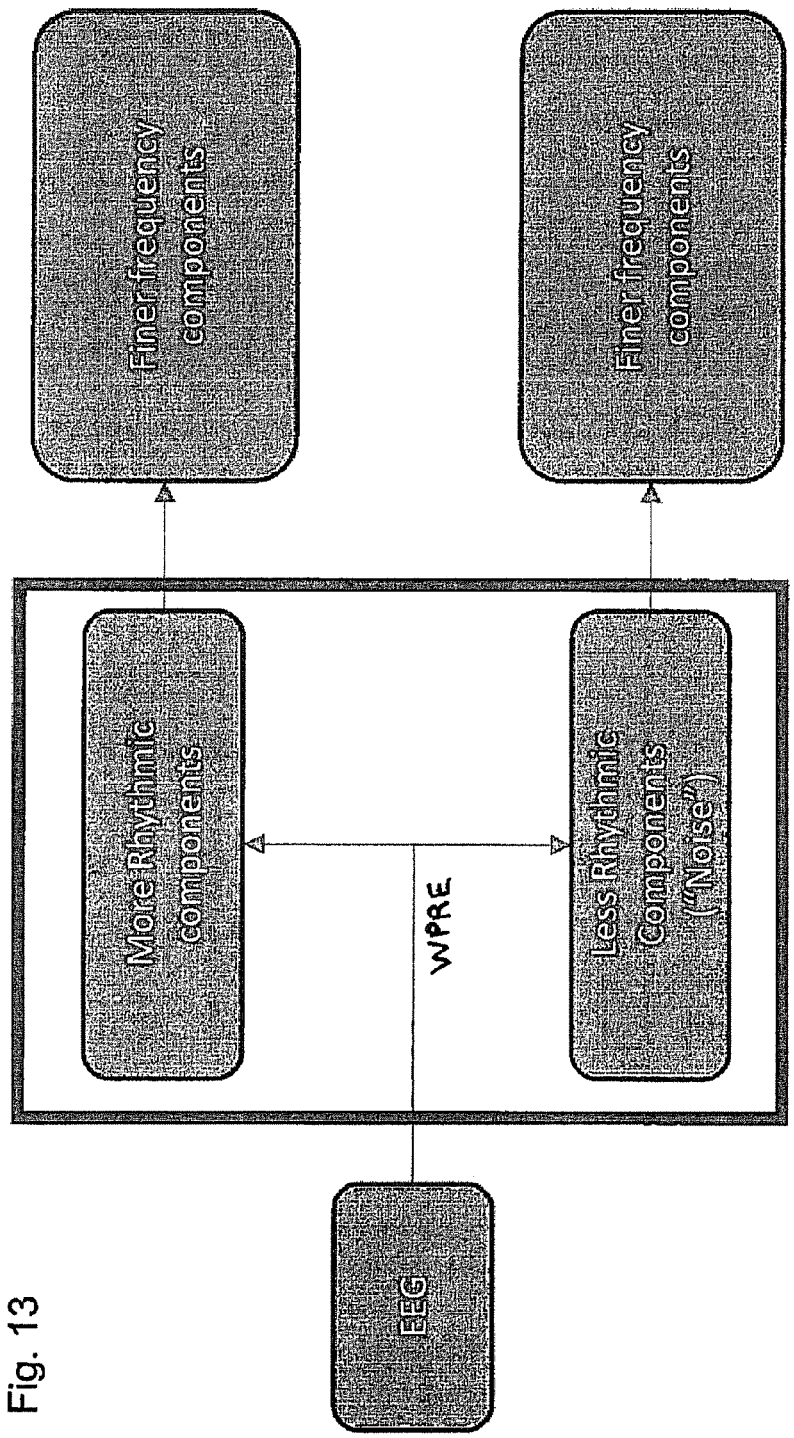
FIG. 13 shows the steps performed during analysis of EEG signals continuously recorded from the six patients undergoing surgery.
Figure 14:
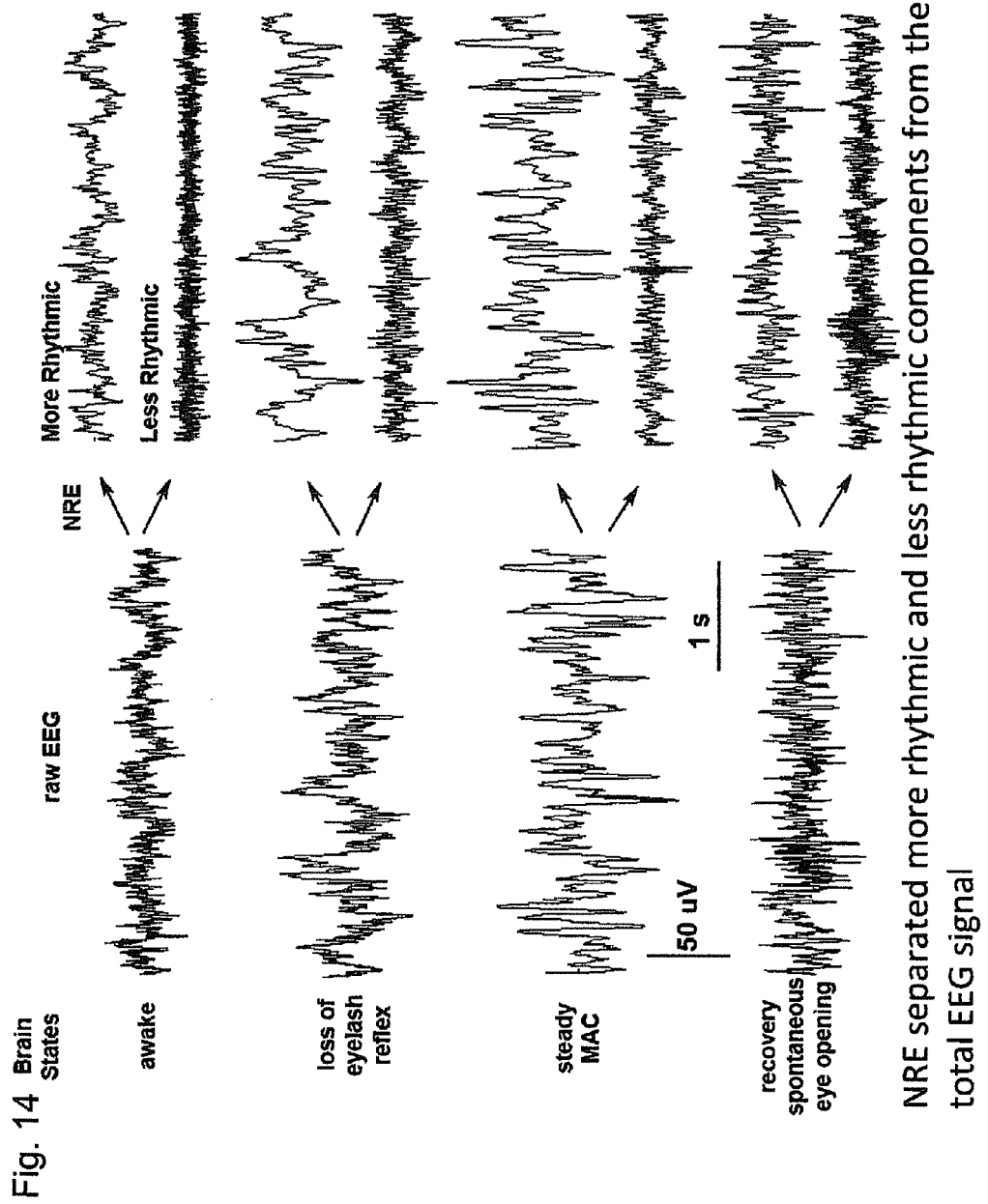
FIG. 14 shows raw EEG signals at different brain stages during the surgery broken down into rhythmic signal and less rhythmic signal components.
Figure 15:
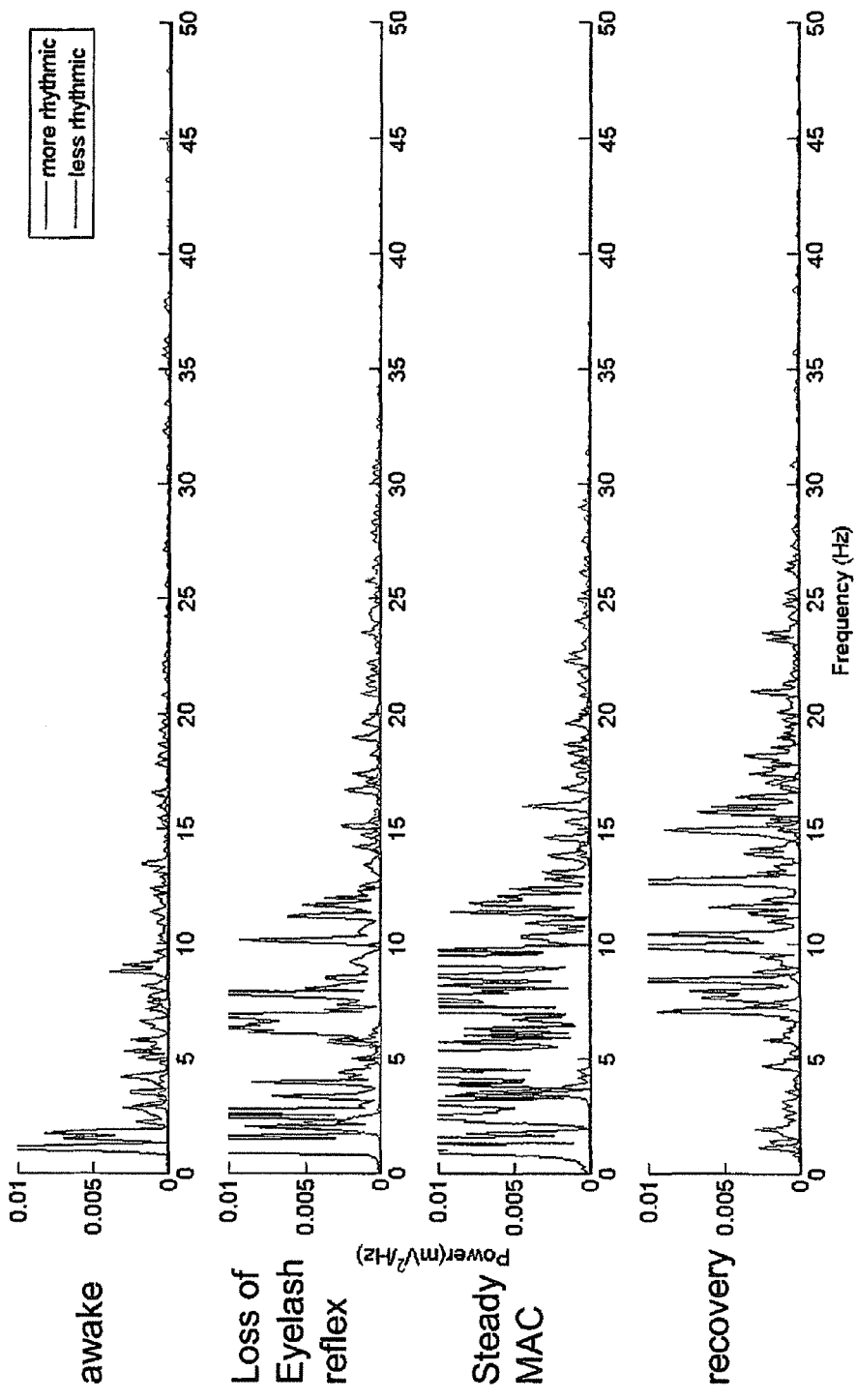
FIG. 15 shows the power spectral components of the rhythmic signal and less rhythmic signal components for each of the brain stages for one of the patients.
Figure 16:
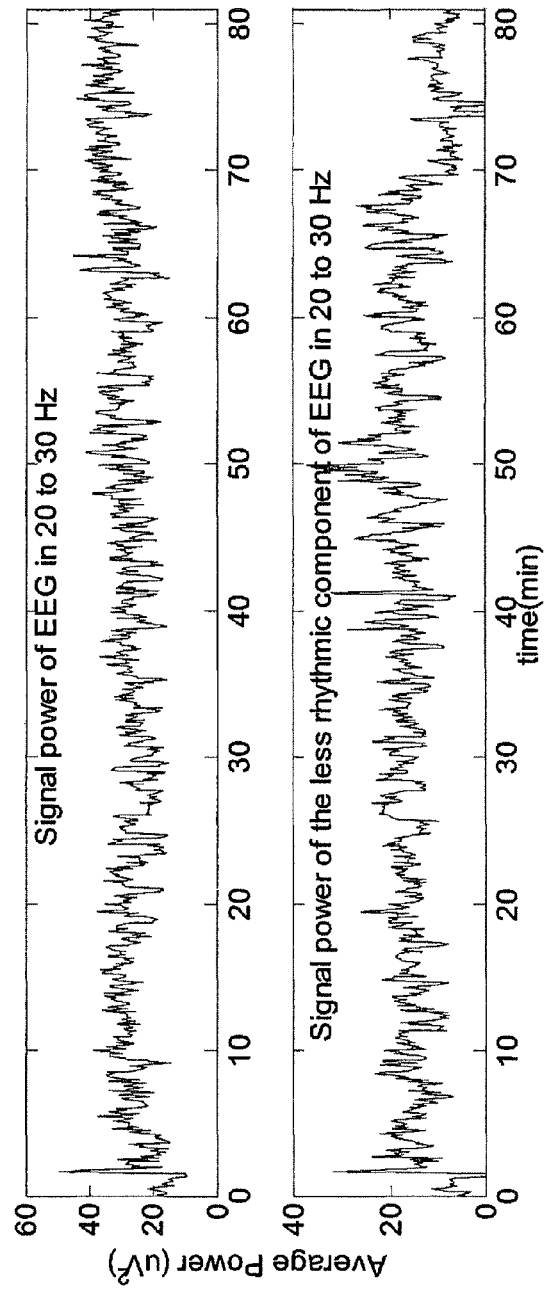
FIG. 16 shows the wavelet transfer function of 20-30 Hz signal components over the course of surgery for one of the patients.

FIG. 9 shows the time series of the Grand Mal seizure EEG signal and a close-up of a segment from time index 6000 to 12000. Below, the WPRE extracted non-rhythmic signal, the WPRE extracted rhythmic signal, and three cases of fine-pruned reconstructions resulting from coefficient magnitude thresholding are shown (with $\kappa$=0.3, 0.5 and 0.8, respectively). As the threshold is increased, fewer coefficients are included in the reconstruction, yielding a sparser representation of the most prominent rhythmic features located within the EEG signal. To achieve a more efficient representation of data for purposes of visualizing and manipulating the coefficients, the wavelet packet analysis tree was condensed following coarse pruning, and the fine-pruning threshold applied to the condensed wavelet packet tree (FIG. 10). This follows from the inherent preservation of information in the wavelet packet analysis tree due to multi-resolution analysis with quadrature mirror filters that allow for perfect reconstruction. Alternatively, the fine pruning may be applied directly to the original wavelet packet analysis tree. FIGS. 11A to 11F illustrate the time-frequency distribution of the wavelet packet coefficients of the condensed wavelet packet analysis tree for a number of manipulations. In particular, FIG. 11A shows the time-frequency distribution of the wavelet packet coefficients of the condensed wavelet packet analysis tree before pruning, FIG. 11B shows the time-frequency distribution of the wavelet packet coefficients of the condensed wavelet packet analysis tree with coarse pruning, and FIGS. 11C to 11F show the time-frequency distribution of the wavelet packet coefficients of the condensed wavelet packet analysis tree with coarse pruning and additional fine pruning with $\kappa$=0.3, 0.5, 0.6 and 0.8, respectively. The grayscale hues in FIGS. 11A to 11F pertain to the relative magnitudes of the coefficients, with darker being greater and lighter being smaller. In an exemplary clinical-related application of the wavelet packet rhythm extraction (WPRE) method, a series of six (6) patients were monitored with EEG and EMG electrodes while undergoing general anesthesia, and it was demonstrated that the subject WPRE method is capable of extracting clinically relevant data in both the more rhythmic and less rhythmic domains, enabling the clinician/anesthetist to better assess the depth of anesthesia (brain state) of the anesthetized individual. FIG. 12 shows the experimental protocol on the six patients undergoing anesthesia. FIG. 13 shows how the EEG data was analyzed by the WPRE method, divided into more rhythmic and less rhythmic signal components and later broken down into specific frequency components. FIG. 14 shows the raw EEG data divided into more rhythmic and less rhythmic signal components at different brain states comprising awake, loss of eyelash reflex (light anesthesia), steady mean alveolar concentration (MAC) in the lungs (deep anesthesia), and early recovery with spontaneous eye opening. A sample of the power spectral components of the more rhythmic and less rhythmic signal components are shown for each of the brain states in FIG. 15, and the wavelet transform of 20-30 Hz signal components over the course of the entire anesthesia for one patient is shown in FIG. 16. FIG. 17 shows the power spectra of the extracted high frequency (>50 Hz) signal components, indicating novel frequency bands around 250 Hz in light anesthesia (loss of eyelash reflex) and around both 250 and 350 Hz in deeper anesthesia, a consistent finding across the six (6) patients undergoing anesthesia. These data show the utility of the subject wavelet packet rhythm extraction method for the elucidation of the depth of anesthesia (brain state) in human subjects.

Figure 18A:
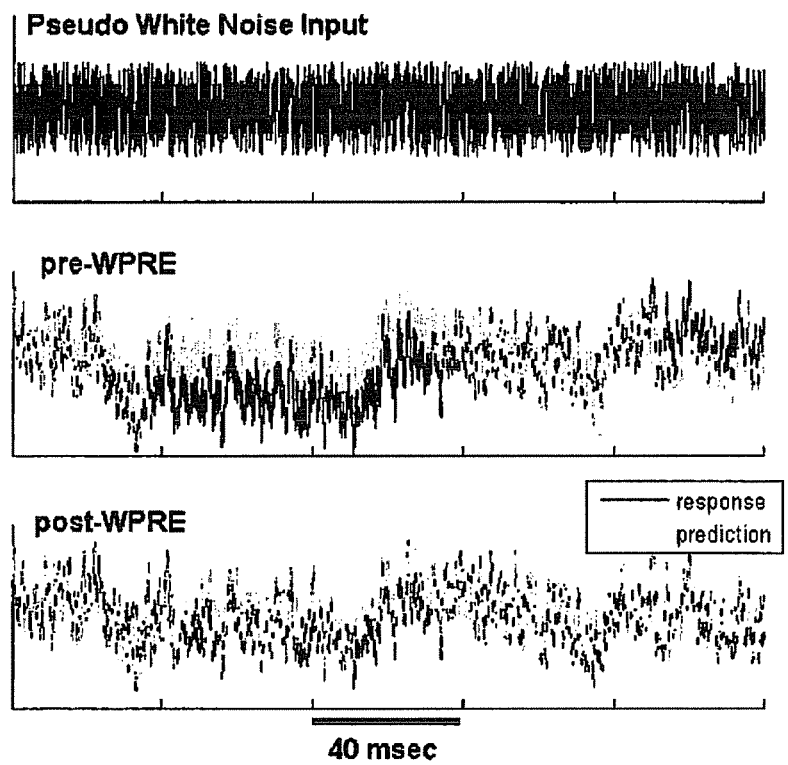
FIG. 18A shows an exemplary nonlinear system identification with input, response and model prediction.
Figure 18B:
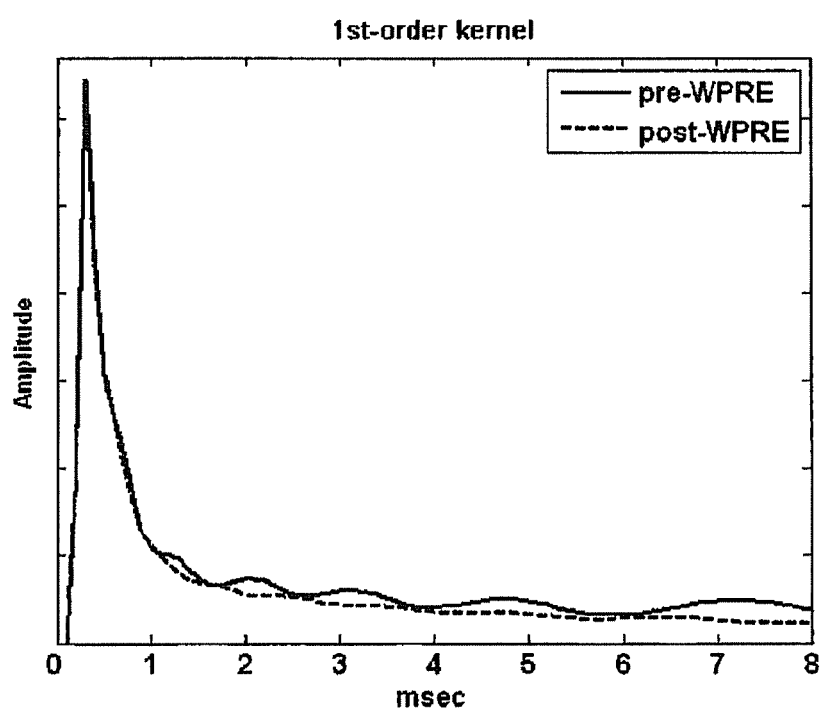
FIG. 18B shows first-order kernel estimates with and without application of the WPRE method before system identification.

The wavelet packet rhythm extraction method discussed above may also be applied to the problem of system identification; in particular, nonlinear system identification (which includes linear system identification as a special case) wherein the dynamic input-output response of a system under examination is characterized by an nth-order functional expansion over a basis of response kernels, an example being the Volterra series. FIGS. 18A and 18B illustrate an example of system identification in which the output response of the system is contaminated with an underlying rhythm that is not associated with the input stimulus. The presence of rhythms or artifacts not related to the input will increase the error in the estimates of the kernels and hence will have a negative impact on the model prediction performance (FIG. 18A). The percent root mean square error of the model versus the prediction in the instance without application of the WPRE method is 28.84%, whereas for the instance following application of the WPRE method and extraction of the underlying rhythm, the error is 9.81%. The estimated first-order kernels are depicted in FIG. 18B, and the ripples in the pre-WPRE kernel associated with the contaminant rhythm are no longer present in the post-WPRE kernel. The estimates of the kernels up to second order were obtain using the Laguerre Expansion Technique (LET) as discussed in the publication entitled "Identification of nonlinear biological systems using Laguerre expansions of kernels" authored by Marmarelis, Ann, Biomed. Eng. 21:573-589, 1993, with the optimal LET parameters selected by minimizing the prediction error in a non-gradient Hooke and Jeeves pattern search of the parameter space.

The wavelet packet rhythm extraction technique and its affiliated techniques can be implemented in software that is run on a general purpose computing device such as for example a personal computer (PC) or other digital electronic hardware or can be implemented on a logic processing device such as for example a field programmable gate array (FPGA) or application specific intergrated circuit (ASIC), for either offline or online processing of complex signals thereby to yield a rhythm signal extractor. The general purpose computing device comprises, for example, a processing unit, system memory (volatile and/or non-volatile memory), other removable or non-removable memory (hard drive, RAM, ROM, EEPROM, CD-ROM, DVD, flash memory, etc.), and a system bus coupling various components to the processing unit. In the software implementation, the processing unit runs program modules including but not limited to routines, programs, object components, data structures etc. that may be embodied as computer readable program code stored on a computer readable medium. A computer readable medium is any data storage device that can store data, which can thereafter be read by a computer system. Examples of computer readable medium include for example read-only memory, random-access memory, flash memory, CD-ROMs, magnetic tape, optical data storage devices and other storage media. The computer readable program code can also be distributed over a network including coupled computer systems so that the computer readable program code is stored and executed in a distributed fashion or copied over a network for local execution. To adapt the WPRE system for online processing, a memory buffer is needed to hold prior samples corresponding to a sufficiently large moving time window (interval) allowing for running computation of the wavelet packet transform and for signal reconstruction. For the specific examples presented in FIGS. 2, 3, and 5 to 11 and 18, the WPRE and affiliated techniques were coded and executed offline in MATLAB™ (The MathWorks, Natick, Mass.) on a 2 GHz AMD Athlon 3800+ personal computer with 2 GB of RAM.

Those of skill in the art will also appreciate that other variations and modifications from those described may be made without departing from the scope and spirit of the invention, as defined by the appended claims.

What is claimed is:

1. A method of detecting and isolating at least one rhythmic signal component from a discrete-time input signal, comprising:
    subjecting the input signal to discrete wavelet packet transform multi-resolution analysis;
    applying wavelet packet basis selection criteria to the result of the analysis, at each stage of the analysis, to evaluate the wavelet packet transform decomposed signal components of the input signal;
    detecting at least one rhythmic signal feature from the input signal based on the evaluation; and
    isolating the detected at least one rhythmic signal feature from the input signal.

2. The method of claim 1 wherein said selection criteria are formulated to evaluate the degree of rhythmicity of the signal components and the average power of the signal components.

3. The method of claim 2 wherein the wavelet packet transform and selection criteria are applied recursively and wherein the degree of rhythmicity of the signal components and the average power of the signal components are evaluated at each level of recursion.

4. The method of claim 3 wherein the degree of rhythmicity is based on interpeak interval variance.

5. The method of claim 4 wherein the degree of rhythmicity is based on normalized interpeak interval variance.

6. The method of claim 1 further comprising processing the detected at least one rhythmic signal feature to isolate individual rhythms or rhythmic components therein.

7. The method of claim 5 wherein said processing comprises pruning wavelet packet coefficient nodes or individual wavelet packet coefficients.

8. The method of claim 1 further comprising detecting and isolating at least two rhythmic signal components from the input signal.

9. The method of claim 8 further comprising processing each detected and isolated rhythmic signal component to isolate individual rhythms or rhythmic components therein.

10. The method of claim 9 wherein said processing comprises pruning wavelet packet coefficient nodes or individual wavelet packet coefficients.

11. The method of claim 9 wherein said processing comprises performing independent component analysis on the isolated at least two rhythmic signal components.

12. The method of claim 9 further comprising combining the isolated at least two rhythmic signal components to form a contiguous rhythm.

13. The method of claim 12 further comprising subjecting at least two contiguous rhythms to independent component analysis.

14. The method of claim 11 wherein independent component analysis is applied to separate at least one rhythmic artifact and at least one genuine source rhythm, if present together.

15. The method of claim 1 further comprising prior to the subjecting, attenuating large spikes or artifacts in the input signal.

16. A method of isolating at least one rhythmic signal component from a discrete-time input signal comprising:
decomposing the input signal using the discrete wavelet packet transform to create a wavelet packet tree;
pruning the wavelet packet tree; and
following pruning, selecting one or more coefficients or coefficient nodes of the wavelet packet tree containing rhythmic signal features thereby to isolate at least one rhythmic signal component of the input signal.

17. The method of claim 16 wherein during pruning, coefficient nodes of the wavelet packet tree below a threshold value are isolated.

18. The method of claim 17 wherein said threshold value is representative of temporal variability of a given time series of the input signal.

19. The method of claim 18 wherein said threshold value is based on the variance of peak-to-peak intervals in the given time series.

20. The method of claim 16 further comprising reconstructing a time series from each selected coefficient or coefficient node.

21. The method of claim 16 further comprising:
ordering the selected coefficients or coefficient nodes according to a metric;
partitioning the ordered coefficients or coefficient nodes;
combining reconstructions of the coefficients or coefficient nodes of the partitions into time series; and
using the time series to construct virtual channels for independent component analysis.

22. The method of claim 21 wherein said metric is frequency.

23. The method of claim 16 further comprising prior to the subjecting, attenuating large spikes or artifacts in the input signal.

24. A method of isolating rhythmic signal features of a discrete-time signal comprising:
subjecting the input signal to wavelet packet transforming and thresholding to evaluate the coefficients or coefficient nodes to be pruned with respect to rhythmicity; and
separating coefficients or coefficient nodes for independent preservation and time series reconstruction of rhythmic signal features.

25. The method of claim 24 wherein said thresholding is based on interpeak interval variance.

26. A computer readable medium embodying computer readable code for detecting and isolating at least one rhythmic component from a discrete-time input signal, said computer readable code comprising:
program code for subjecting the input signal to discrete wavelet packet transform multi-resolution analysis;
program code for applying wavelet packet basis selection criteria to the result of the analysis, at each stage of the analysis, to evaluate the wavelet packet decomposed signal components of the input signal;
program code for detecting at least one rhythmic signal component based on the evaluation; and
program code for isolating the detected at least one rhythmic signal component from the input signal.

27. A computer readable medium embodying computer readable code for isolating at least one rhythmic signal component from a discrete-time input signal comprising:
program code for decomposing the input signal using the discrete wavelet packet transform to create a wavelet packet tree;
program code for pruning the wavelet packet tree; and
program code for, following pruning, selecting one or more coefficients or coefficient nodes of the wavelet packet tree containing rhythmic signal features thereby to isolate at least one rhythmic signal component of the input signal.

28. A computer readable medium embodying computer readable code for isolating rhythmic signal features of a discrete-time signal comprising:
program code for subjecting the input signal to wavelet packet transforming and thresholding to evaluate the coefficients or coefficient nodes to be pruned with respect to rhythmicity; and
program code for separating coefficients or coefficient nodes for independent preservation and time series reconstruction of rhythmic signal features.

29. A rhythmic signal extractor for detecting and isolating at least one rhythmic signal component from a discrete-time input signal, comprising:
a discrete wavelet packet transform multi-resolution analyzer for analyzing the input signal and evaluating rhythmic signal features of the input signal; and
a signal component isolator for isolating at least one rhythmic signal component from the input signal based on the evaluation.

* * * * *